US012649669B2

(12) United States Patent
Ansari et al.

(10) Patent No.: US 12,649,669 B2
(45) Date of Patent: *Jun. 9, 2026

(54) METHOD FOR MICROORGANISM GROWTH INHIBITION

(71) Applicant: Imam Abdulrahman Bin Faisal University, Dammam (SA)

(72) Inventors: Mohammad Azam Ansari, Dammam (SA); Abdulhadi Baykal, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 285 days.

This patent is subject to a terminal disclaimer.

(21) Appl. No.: 18/399,841

(22) Filed: Dec. 29, 2023

(65) Prior Publication Data

US 2024/0182321 A1     Jun. 6, 2024

Related U.S. Application Data

(60) Continuation of application No. 17/203,835, filed on Mar. 17, 2021, now Pat. No. 11,891,308, which is a
(Continued)

(51) Int. Cl.
*C01G 37/00* (2006.01)
*A61L 2/18* (2026.01)
(Continued)

(52) U.S. Cl.
CPC .............. *C01G 37/006* (2013.01); *A61L 2/18* (2013.01); *A61L 2/232* (2013.01); *B82Y 30/00* (2013.01);
(Continued)

(58) Field of Classification Search
CPC ......... C01G 37/006; A61L 2/18; A61L 2/232; B82Y 30/00; B82Y 40/00; C01P 2002/32; C01P 2002/72; C01P 2002/82
See application file for complete search history.

(56) References Cited

U.S. PATENT DOCUMENTS

| | | | |
|---|---|---|---|
| 4,025,449 | A | 5/1977 | Pezzoli |
| 7,326,360 | B1 | 2/2008 | Jiles et al. |

(Continued)

FOREIGN PATENT DOCUMENTS

| | | |
|---|---|---|
| CN | 1807672 A | 7/2006 |
| CN | 100386461 C | 5/2008 |
| CN | 107442065 A | 12/2017 |

OTHER PUBLICATIONS

Noppakun Sanpo, et al., "Sol-Gel Synthesized Copper-Substituted Cobalt Ferrite Nanoparticles for Biomedical Applications", Journal of Nano Research, vol. 22, May 2013, pp. 95-106.
(Continued)

*Primary Examiner* — Blessing M Fubara

(74) *Attorney, Agent, or Firm* — Oblon, McClelland, Maier & Neustadt, L.L.P.

(57) ABSTRACT

Methods of forming spinel ferrite nanoparticles containing a chromium-substituted copper ferrite as well as properties (e.g. particle size, crystallite size, pore size, surface area) of these spinel ferrite nanoparticles are described. Methods of preventing or reducing microbe growth on a surface by applying these spinel ferrite nanoparticles onto the surface in the form of a suspension or an antimicrobial product are also described.

12 Claims, 13 Drawing Sheets

Related U.S. Application Data division of application No. 16/250,626, filed on Jan. 17, 2019, now Pat. No. 11,643,335.

(51) Int. Cl.
    *A61L 2/232* (2006.01)
    *B82Y 30/00* (2011.01)
    *B82Y 40/00* (2011.01)

(52) U.S. Cl.
    CPC ........... *B82Y 40/00* (2013.01); *C01P 2002/32* (2013.01); *C01P 2002/72* (2013.01); *C01P 2002/82* (2013.01)

(56) References Cited

U.S. PATENT DOCUMENTS

| | | | | |
|---|---|---|---|---|
| 11,643,335 | B2 * | 5/2023 | Ansari | A61L 2/232 424/405 |
| 11,753,310 | B2 * | 9/2023 | Ansari | H01F 1/0054 424/405 |
| 11,891,308 | B2 * | 2/2024 | Ansari | H01F 1/344 |
| 12,006,226 | B2 * | 6/2024 | Ansari | H01F 1/344 |
| 12,227,429 | B2 * | 2/2025 | Ansari | A61L 2/232 |
| 2019/0134151 | A1 | 5/2019 | Bond | |
| 2023/0202860 | A1 | 6/2023 | Ansari | |

OTHER PUBLICATIONS

D. M. Borikar, et al., "Synthesis of nanosized chromium substituted copper spinel ferrite", International Journal of Researches in Biosciences, Agriculture & Technology, Issue 2, Feb. 2015, pp. 169-173.

S. Asiri, et al., "Magneto-optical properties of $BaCr_yFe_{12-y}O_{19}$ ($0.0 \leq y \leq 1.0$) hexaferrites", Journal of Magnetism and Magnetic Materials, vol. 451, 2018, pp. 463-472.

K. G. Rewatkar, et al., "Structural and Electrical Characterization of Chromium Substituted Copper Spinel Ferrite", Journal of Scientific and Technical Research, vol. 4, Issue 2, 2017, 1 page (Abstract only).

Borikar et al. Synthesis of nanosized chromium substituted copper spinel ferrite [online],Feb. 2015.

Sanpo et al. (Acta Biomaterialia 9(2013) 5830-5837) (Year: 2013).

Ansari et al. (Journal of Inorganic and Organometallic Polymers and Materials (2018) 28:231602327) (Year: 2018).

Borikar et al. (International Journal of Researches In Bioscience, Agriculture & Technology; Special Issue 2, pp. 1690173, 2015,). (Year: 2015).

* cited by examiner

METHOD FOR MICROORGANISM GROWTH INHIBITION

CROSS-REFERENCE TO RELATED APPLICATIONS

The present application is a Continuation of U.S. application Ser. No. 17/203,835, now allowed, having a filing date of Mar. 17, 2021 which is a Division of U.S. application Ser. No. 16/250,626, now U.S. Pat. No. 11,643,335, having a filing date of Jan. 17, 2019.

STATEMENT REGARDING PRIOR DISCLOSURE BY THE INVENTORS

Aspects of this technology are described in an article "Synthesis and Characterization of Antibacterial Activity of Spinel Chromium-Substituted Copper Ferrite Nanoparticles for Biomedical Application" published in Journal of Inorganic and Organometallic Polymers and Materials, 2018, Volume 28, Issue 6, pp 2316-2327, on Jun. 6, 2018, which is incorporated herein by reference in its entirety.

BACKGROUND OF THE INVENTION

Technical Field

The present disclosure relates to spinel ferrite nanoparticles comprising a chromium-substituted copper ferrite, a method of preparing the spinel ferrite nanoparticles, and methods of utilizing these spinel ferrite nanoparticles for killing or inhibiting growth of microorganisms and sterilizing surfaces contaminated with biologically active pathogens and/or microorganisms.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Nanotechnology research came to prominence in the 21$^{st}$ century as it became increasingly important for a broad range of practical applications. Ferrite nanoparticles have attracted much attention because of their superparamagnetic properties as well as large surface area to volume ratio, which are different from their bulk counterparts [Naseri M G, Saion E B, Ahangar H A, Shaari A H, Hashim M. Simple synthesis and characterization of cobalt ferrite nanoparticles by a thermal treatment method. Journal of Nanomaterials. 2010, 1; 2010:75; and Kefeni K K, Mamba B B, Msagati T A. Application of spinel ferrite nanoparticles in water and wastewater treatment: a review. Separation and Purification Technology. 2017, 188:399-422, each incorporated herein by reference in their entirety]. Ferrites are classified as spinel, garnet, hexaferrite or orthoferrite according to their crystal structures and magnetic properties [Singh R, Thirupathi G. Manganese-Zinc Spinel Ferrite Nanoparticles and Ferrofluids. In Magnetic Spinels-Synthesis, Properties and Applications 2017. Chapter 7, InTech. doi.org/10.5772/66522, pages 140-159]. Recently, special attention has been given to transition metal ferrite nanoparticles with spinel structures because of their renowned magnetic, catalytic, optical, and electronic properties and high adsorption capability [Sanpo N, Wen C, Berndt C C, Wang J. Antibacterial properties of spinel ferrite nanoparticles. Microbial pathogens and strategies for combating them: science, technology and education. Spain: Formatex Research Centre. 2013:239-50, incorporated herein by reference in its entirety]. In addition, because of their high permeability and good saturation magnetization, these transition metal ferrite nanoparticles are magnetically soft and readily magnetized and demagnetized [Mathew T, Malwadkar S, Shivanand, Pai, Sharanappa N, Sebastian C P. Oxidative dehydrogenation of ethylbenzene over $Cu_{1-x}Co_xFe_2O_4$ catalyst system: Influence of acid-base property. Catalysis Letters. 2003; 91:217-24, incorporated herein by reference in its entirety].

Properties of ferrite nanoparticles may be tuned by modifying their particle size, shape, and the amount of substituted transition metal ions. Spinel ferrite nanoparticles might be used in biomedicine for cancer treatment [Peng Y, Wang Z, Liu W, Zhang H, Zuo W, Tang H, Chen F, Wang B. Size- and shape-dependent peroxidase-like catalytic activity of $MnFe_2O_4$ Nanoparticles and their applications in highly efficient colorimetric detection of target cancer cells. Dalton Transactions. 2015; 44 (28):12871-7, incorporated herein by reference in its entirety], dopamine investigation [Reddy S, Swamy B K, Chandra U, Mahathesha K R, Sathisha T V, Jayadevappa H. Synthesis of $MgFe_2O_4$ nanoparticles and $MgFe_2O_4$ nanoparticles/CPE for electrochemical investigation of dopamine. Analytical Methods. 2011, 3 (12): 2792-6, incorporated herein by reference in its entirety], magnetic hyperthermia for diagnosis and treatment of cancer, drug delivery, cellular signaling, and magnetic resonance imaging [Céspedes E, Byrne J M, Farrow N, Moise S, Coker V S, Bencsik M, Lloyd J R, Telling N D. Bacterially synthesized ferrite nanoparticles for magnetic hyperthermia applications. Nanoscale. 2014, 6 (21):12958-70; and Choi H, Lee S, Kouh T, Kim S J, Kim C S, Hahn E. Synthesis and characterization of Co—Zn ferrite nanoparticles for application to magnetic hyperthermia. Journal of the Korean Physical Society. 2017, 70 (1):89-92, each incorporated herein by reference in their entirety]. They may also be used for magnetic recording [Shu C, Qiao H. Tuning Magnetic Properties of Magnetic Recording Media Cobalt Ferrite Nano-Particles by Co-Precipitation Method. In Photonics and Optoelectronics, 2009. SOPO 2009. Symposium on 2009, pp. 1-4. IEEE, incorporated herein by reference in its entirety], catalysis [Zhang L, Wu Y. Sol-Gel synthesized magnetic $MnFe_2O_4$ spinel ferrite nanoparticles as novel catalyst for oxidative degradation of methyl orange. Journal of Nanomaterials. 2013, 1; 2013:2; and Waag F, Gökce B, Kalapu C, Bendt G, Salamon S, Landers J, Hagemann U, Heidelmann M, Schulz S, Wende H, Hartmann N. Adjusting the catalytic properties of cobalt ferrite nanoparticles by pulsed laser fragmentation in water with defined energy dose. Scientific Reports. 2017, 7 (1):13161, each incorporated herein by reference in their entirety], sensing [Joshi S, Kamble V B, Kumar M, Umarji A M, Srivastava G. Nickel substitution induced effects on gas sensing properties of cobalt ferrite nanoparticles. Journal of Alloys and Compounds. 2016, 654:460-6; and Zafar Q, Azmer M I, Al-Sehemi A G, Al-Assiri M S, Kalam A, Sulaiman K. Evaluation of humidity sensing properties of TMBHPET thin film embedded with spinel cobalt ferrite nanoparticles. Journal of Nanoparticle Research. 2016, 18 (7):186, each incorporated herein by reference in their entirety], water and wastewater treatment [Kefeni K K, Mamba B B, Msagati T A. Application of spinel ferrite nanoparticles in water and wastewater treatment: a review. Separation and Purification Technology. 2017, 188:399-422], magneto-optical devices, heat absorbers and generators, energy storage, electromagnetic interference shielding, and microwave devices [Singh R, Thirupathi G. Manganese-Zinc Spinel Ferrite Nanoparticles and Ferrofluids. In Magnetic Spinels-Synthesis, Properties and Applications 2017. Chapter 7, InTech. doi.org/10.5772/66522 pages 140-159; and Kefeni K K, Msagati T A, Mamba B B. Ferrite nanoparticles: synthesis, characterisation and applications in electronic device. Materials Science and Engineering: B. 2017, 215:37-55, each incorporated herein by reference in their entirety]. Spinel ferrite nanoparticles can be synthesized by methods such as auto combustion [Velhal N B, Patil N D, Shelke A R, Deshpande N G, Puri V R. Structural, dielectric and magnetic properties of nickel substituted cobalt ferrite nanoparticles: Effect of nickel concentration. AIP Advances. 2015, 5 (9): 097166, incorporated herein by reference in its entirety], polymeric precursor methods [Gharagozlou M. Synthesis, characterization and influence of calcination temperature on magnetic properties of nanocrystalline spinel Co-ferrite prepared by polymeric precursor method," Journal of Alloys and Compounds. 2009, 486:660-665, incorporated herein by reference in its entirety], sonochemical processes [Shafi K V, Gedanken A, Prozorov R, Balogh J. Sonochemical preparation and size-dependent properties of nanostructured $CoFe_2O_4$ particles. Chemistry of Materials. 1998, 10 (11):3445-50, incorporated herein by reference in its entirety], microemulsions [Vestal C R, Zhang Z J. Synthesis of $CoCrFeO_4$ nanoparticles using microemulsion methods and size-dependent studies of their magnetic properties. Chemistry of materials. 2002, 14 (9):3817-22, incorporated herein by reference in its entirety], pulsed laser ablation in liquid [Waag F, Gökce B, Kalapu C, Bendt G, Salamon S, Landers J, Hagemann U, Heidelmann M, Schulz S, Wende H, Hartmann N. Adjusting the catalytic properties of cobalt ferrite nanoparticles by pulsed laser fragmentation in water with defined energy dose. Scientific Reports. 2017, 7 (1):13161, incorporated herein by reference in its entirety], ball milling [Khedr M H, Omar A A, Abdel-Moaty S A. Magnetic nanocomposites: preparation and characterization of Co-ferrite nanoparticles. Colloids and surfaces A: Physicochemical and engineering aspects. 2006, 281 (1-3):8-14, incorporated herein by reference in its entirety], co-precipitation [Dabagh S, Chaudhary K, Haider Z, Ali J. Study of structural phase transformation and hysteresis behavior of inverse-spinel α-ferrite nanoparticles synthesized by co-precipitation method. Results in Physics. 2018, 8:93-8; and Rani B J, Ravina M, Saravanakumar B, Ravi G, Ganesh V, Ravichandran S, Yuvakkumar R. Ferrimagnetism in cobalt ferrite ($CoFe_2O_4$) nanoparticles. Nano-Structures & Nano-Objects. 2018, 14:84-91, each incorporated herein by reference in their entirety], hydrothermal [Zhang W, Zuo X, Zhang D, Wu C, Silva S R. Cr3+ substituted spinel ferrite nanoparticles with high coercivity. Nanotechnology. 2016, 27 (24):245707, incorporated herein by reference in its entirety], sol-gel [Ashour A H, El-Batal Al, Abdel Maksoud M I A, El-Sayyad G S, Labibc S, Abdeltwab E, El-Okr M M. Antimicrobial activity of metal-substituted cobalt ferrite nanoparticles synthesized by sol-gel technique. Particuology. 2018; volume 40, pages 141-151, incorporated herein by reference in its entirety], solvothermal [Kalam A, Al-Sehemi A G, Assiri M, Du G, Ahmad T, Ahmad I, Pannipara M. Modified Solvothermal synthesis of cobalt ferrite ($CoFe_2O_4$) magnetic nanoparticles photocatalysts for degradation of methylene blue with $H_2O_2$/visible light. Results in Physics. 2018 Jan. 31, incorporated herein by reference in its entirety], aerosol spray pyrolysis methods [Hong D, Yamada Y, Sheehan M, Shikano S, Kuo C H, Tian M, Tsung C K, Fukuzumi S. Mesoporous nickel ferrites with spinel structure prepared by an aerosol spray pyrolysis method for photocatalytic hydrogen evolution. ACS Sustainable Chemistry & Engineering. 2014, 2 (11): 2588-94, incorporated herein by reference in its entirety], reverse micelles [Morrison S A, Cahill C L, Carpenter E E, Calvin S, Harris V G. Preparation and characterization of MnZn-ferrite nanoparticles using reverse micelles. Journal of applied physics. 2003, 93 (10):7489-91, incorporated herein by reference in its entirety], and biogenic methods using bacteria such as *Geobacter sulfurreducens* [Cespedes E, Byrne J M, Farrow N, Moise S, Coker V S, Bencsik M, Lloyd J R, Telling N D. Bacterially synthesized ferrite nanoparticles for magnetic hyperthermia applications. Nanoscale. 2014, 6 (21):12958-70, incorporated herein by reference in its entirety].

Antimicrobial activities of several metal and metal oxide nanoparticles including silver [Ali S G, Ansari M A, Khan H M, Jalal M, Mahdi A A, Cameotra S S. Antibacterial and Antibiofilm Potential of Green Synthesized Silver Nanoparticles against Imipenem Resistant Clinical Isolates of *P. aeruginosa*. BioNanoScience. 2018:1-0, incorporated herein by reference in its entirety], gold [Payne J N, Waghwani H K, Connor M G, Hamilton W, Tockstein S, Moolani H, Chavda F, Badwaik V, Lawrenz M B, Dakshinamurthy R. Novel synthesis of kanamycin conjugated gold nanoparticles with potent antibacterial activity. Frontiers in microbiology. 2016, 7:607, incorporated herein by reference in its entirety], ZnO [Jalal M, Ansari M A, Ali S G, Khan H M, Rehman S. Anticandidal activity of bioinspired ZnO NPs: effect on growth, cell morphology and key virulence attributes of *Candida* species. Artificial cells, nanomedicine, and biotechnology. 2018, 14:1-4, incorporated herein by reference in its entirety], $Al_2O_3$ [Ansari M A, Khan H M, Alzohairy M A, Jalal M, Ali S G, Pal R, Musarrat J. Green synthesis of $Al_2O_3$ nanoparticles and their bactericidal potential against clinical isolates of multi-drug resistant *Pseudomonas aeruginosa*. World Journal of Microbiology and Biotechnology. 2015, 31(1):153-64, incorporated herein by reference in its entirety], $Fe_3O_4$ [Arakha M, Pal S, Samantarrai D, Panigrahi T K, Mallick B C, Pramanik K, Mallick B, Jha S. Antimicrobial activity of iron oxide nanoparticle upon modulation of nanoparticle-bacteria interface. Scientific reports. 2015, 5:14813; and Nehra P, Chauhan R P, Garg N, Verma K. Antibacterial and antifungal activity of chitosan coated iron oxide nanoparticles. British journal of biomedical science. 2018, 75(1):13-8, each incorporated herein by reference in their entirety], and magnetic iron oxide α-$Fe_2O_3$ [Ismail R A, Sulaiman G M, Abdulrahman S A, Marzoog T R. Antibacterial activity of magnetic iron oxide nanoparticles synthesized by laser ablation in liquid. Materials Science and Engineering: C. 2015, 53:286-97, incorporated herein by reference in its entirety] nanoparticles have been reported. However, very little information is available regarding the antibacterial properties of transition metal substituted spinel ferrite nanoparticles. Recently, Sanpo et al. [Sanpo N, Wen C, Berndt C C, Wang J. Antibacterial properties of spinel ferrite nanoparticles. Microbial pathogens and strategies for combating them: science, technology and education. Spain: Formatex Research Centre. 2013:239-50, incorporated herein by reference in its entirety], Samavati and Ismail et al. [Samavati A, Ismail A F. Antibacterial properties of copper-substituted cobalt ferrite nanoparticles synthesized by co-precipitation method. Particuology. 2017; 30:158-63, incorporated herein by reference in its entirety], and Ashour et al. [Ashour A H, El-Batal A I, Abdel Maksoud M I A, El-Sayyad G S, Labibc S. Abdeltwab E, El-Okr M M. Antimicrobial activity of metal-substituted cobalt ferrite nanoparticles synthesized by sol-gel technique. Particuology. 2018; volume 40, pages 141-151, incorporated herein by reference in its entirety] investigated antibacterial activities of copper, zinc, nickel, and manganese substituted cobalt ferrite nanoparticles for preventing microbial infections.

In view of the forgoing, one objective of the present disclosure is to provide a method of making spinel ferrite nanoparticles comprising a chromium-substituted copper ferrite. Another objective of the present disclosure is to provide a method of preventing or reducing microbial growth on a surface by applying spinel ferrite nanoparticles to the surface.

BRIEF SUMMARY OF THE INVENTION

According to a first aspect, the present disclosure relates to a method of making spinel ferrite nanoparticles comprising a chromium-substituted copper ferrite of formula (I), $$CuCr_xFe_{2-x}O_4 \qquad (I)$$

wherein x is greater than 0 and smaller than 2. The method involves the steps of mixing a copper(II) salt, a chromium (III) salt, an iron(III) salt, an inorganic base, and water to form a mixture, heating the mixture to form a precipitate, and drying the precipitate, thereby producing the spinel ferrite nanoparticles.

In one embodiment, the inorganic base is sodium hydroxide.

In one embodiment, the mixture has a pH in a range of 10-12.

In one embodiment, the mixture is heated at a first temperature of 40-100° C. for 0.1-3 hours, and subsequently at a second temperature of 110-180° C. for 1-6 hours.

In one embodiment, the precipitate is dried at a temperature of 40-100° C. for 1-24 hours.

In one embodiment, the copper(II) salt is copper(II) nitrate.

In one embodiment, the chromium(III) salt is chromium (III) chloride.

In one embodiment, the iron(III) salt is iron(III) nitrate.

In one embodiment, the chromium-substituted copper ferrite of formula (I) is at least one selected from the group consisting of $CuCr_{0.2}Fe_{1.8}O_4$, $CuCr_{0.4}Fe_{1.6}O_4$, $CuCr_{0.6}Fe_{1.4}O_4$, $CuCr_{0.8}Fe_{1.2}O_4$, and $CuCrFeO_4$.

In one embodiment, the spinel ferrite nanoparticles have an average particle size in a range of 20-90 nm.

In one embodiment, the spinel ferrite nanoparticles are porous.

In one embodiment, the spinel ferrite nanoparticles have a BET surface area in a range of 8-30 m²/g.

In one embodiment, the spinel ferrite nanoparticles have an optical band gap energy value of 1.0-2.0 eV.

According to a second aspect, the present disclosure relates to a method for preventing or reducing growth of a microorganism on a surface. The method involves applying spinel ferrite nanoparticles onto the surface, wherein (i) the spinel ferrite nanoparticles comprise a chromium-substituted copper ferrite of formula (I)

$$CuCr_xFe_{2-x}O_4 \qquad (I)$$

wherein x is greater than 0 and smaller than 2, and (ii) the spinel ferrite nanoparticles are in contact with the surface for 0.1-24 hours.

In one embodiment, the spinel ferrite nanoparticles have an average particle size in a range of 20-90 nm.

In one embodiment, the spinel ferrite nanoparticles are applied onto the surface as a suspension comprising a solvent and 50 μg/mL to 100 mg/mL of the spinel ferrite nanoparticles relative to a total volume of the suspension.

In one embodiment, the solvent comprises water.

In one embodiment, the microorganism is a gram-negative bacterium.

In one embodiment, the gram-negative bacterium is *Escherichia coli.*

According to a third aspect, the present disclosure relates to spinel ferrite nanoparticles, comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figures 1A, 1B, 1C:
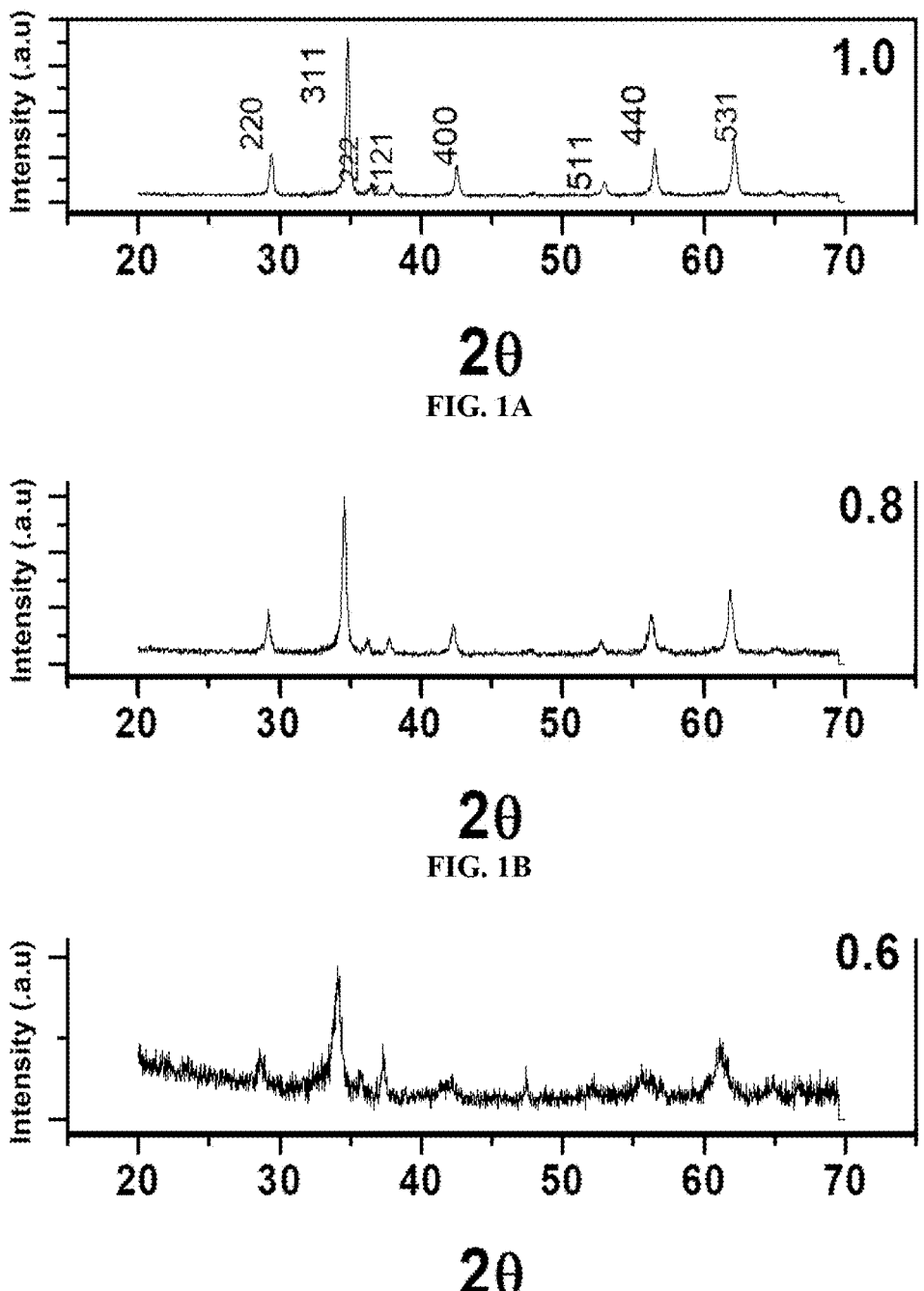
FIG. 1A shows X-ray diffraction (XRD) patterns of spinel ferrite nanoparticles containing $CuCrFeO_4$.
FIG. 1B shows XRD patterns of spinel ferrite nanoparticles containing $CuCr_{0.8}Fe_{1.2}O_4$.
FIG. 1C shows XRD patterns of spinel ferrite nanoparticles containing $CuCr_{0.6}Fe_{1.4}O_4$.
Figure 1D:
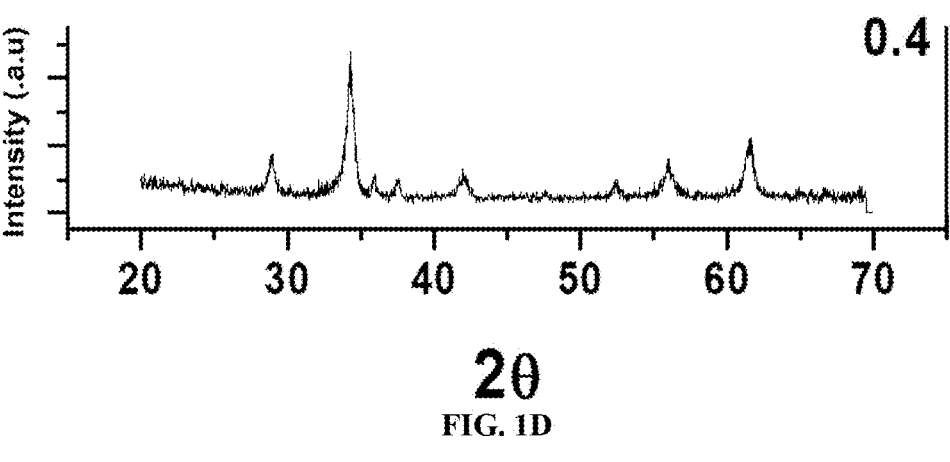
FIG. 1D shows XRD patterns of spinel ferrite nanoparticles containing $CuCr_{0.4}Fe_{1.6}O_4$.
Figure 1E:
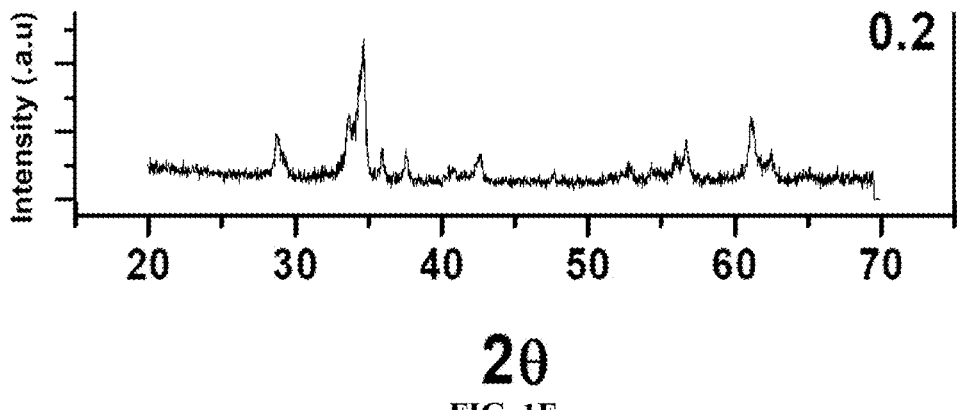
FIG. 1E shows XRD patterns of spinel ferrite nanoparticles containing $CuCr_{0.2}Fe_{1.8}O_4$.
Figure 1F:
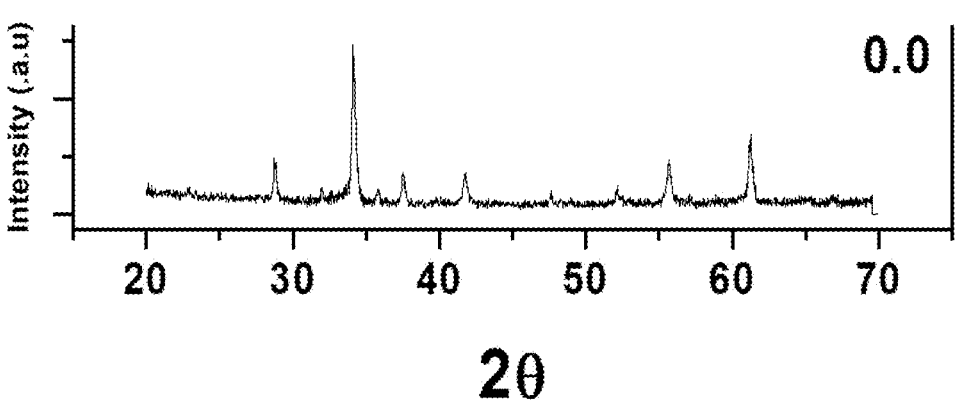
FIG. 1F shows XRD patterns of spinel ferrite nanoparticles containing $CuFe_2O_4$.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "compound" and "product" are used interchangeably, and are intended to refer to a chemical entity, whether in the solid, liquid or gaseous phase, and whether in a crude mixture or purified and isolated.

As used herein, a salt refers to an ionic compound derivable from the neutralization reaction of an acid and a base. Salts are composed of related numbers of cations (positively charged ions) and anions (negatively charged ions) such that the product is electrically neutral (without a net charge). These component ions may be inorganic (e.g. chloride, $Cl^-$) or organic (e.g. acetate, $CH_3CO_2^-$) and may be monoatomic (e.g. fluoride, $F^-$) or polyatomic (e.g. sulfate, $SO_4^{2-}$). Exemplary conventional salts include, but are not limited to, those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and mixtures and hydrates thereof and the like. The present disclosure includes all hydration states of a given salt or formula, unless otherwise noted. For example, copper(II) nitrate includes anhydrous $Cu(NO_3)_2$, monohydrate $Cu(NO_3)_2 \cdot H_2O$, hemi(pentahydrate) $Cu(NO_3)_2 \cdot 2.5H_2O$, trihydrate $Cu(NO_3)_2 \cdot 3H_2O$), and any other hydrated forms or mixtures. Chromium(III) chloride includes anhydrous $CrCl_3$, and hydrated forms such as chromium trichloride hexahydrate $CrCl_3 \cdot 6H_2O$. Iron(III) nitrate includes anhydrous $Fe(NO_3)_3$, and hydrated forms such as iron(III) nitrate nonahydrate $Fe(NO_3)_3 \cdot 9H_2O$.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of oxygen include $^{16}O$, $^{17}O$, and $^{18}O$, isotopes of copper include $^{63}Cu$ and $^{65}Cu$, isotopes of chromium include $^{50}Cr$, $^{52}Cr$, $^{53}Cr$, and $^{54}Cr$, and isotopes of iron include $^{54}Fe$, $^{56}Fe$, $^{57}Fe$, and $^{58}Fe$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

A first aspect of the present disclosure relates to a method of making spinel ferrite nanoparticles comprising a chromium-substituted copper ferrite of formula (I), $$CuCr_xFe_{2-x}O_4 \qquad (I)$$

wherein x is greater than 0) and smaller than 2, preferably x is in a range of $0<x\le1.5$, more preferably x is in a range of $0.1\le x\le1.0$. The method involves the steps of mixing a copper(II) salt, a chromium(III) salt, an iron(III) salt, an inorganic base, and water to form a mixture, heating the mixture to form a precipitate, and drying the precipitate, thereby producing the spinel ferrite nanoparticles.

As defined herein, a spinel is a metal oxide compound with a general formula $A^{2+}B_2^{3+}O_4^{2-}$, where "A" and "B" are metal ions. In one embodiment, "A" may be Zn, Cu, Co, Mn, Ni, Mg, Be, and/or Ti, and "B" may be Al, Fe, Cr, and/or V. Preferably, spinel compounds are in the form of crystals, with the oxide anions arranged in a cubic close-packed lattice, and with the metal ions occupying octahedral and/or tetrahedral sites within the lattice. Preferably, the $A^{2+}$ metal ions occupy the tetrahedral sites, and the $B^{3+}$ metal ions occupy the octahedral sites, though there may be instances where the metal ions are switched. The $A^{2+}$ and $B^{3+}$ metal ions may occupy sites in the lattice at regular spacings or may be distributed randomly. A spinel ferrite is defined herein as an iron-containing spinel compound with a formula $C^{2+}D_{2-y}^{3+}Fe_yO_4^{2-}$, where "C" and "D" are metal ions, and "y" is in a range of $0\le y\le2$. In one embodiment, "C" may be Zn, Cu, Co, Mn, Ni, Mg, Be, and/or Ti, and "D" may be Al, Fe, Cr, and/or V. Preferably, the tetrahedral sites of a spinel ferrite are occupied by $C^{2+}$ metal ions, and the octahedral sites are occupied by $Fe^{3+}$ ions and substitution $D^{3+}$ metal ions.

In one or more embodiments, the spinel ferrite disclosed herein comprises a chromium-substituted copper ferrite of formula (I), $$CuCr_xFe_{2-x}O_4 \qquad (I)$$

wherein x is greater than 0 and smaller than 2, preferably x is in a range of $0<x\le1.5$, more preferably x is in a range of $0.1\le x\le1.0$. For example, x may be 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1. Alternatively, x may be 1.1, 1.2, 1.3, 1.4, 1.5, 1.6, 1.7, 1.8, or 1.9. In preferred embodiments, x is 0.2, 0.4, 0.6, 0.8, or 1. In a related embodiment, the spinel ferrite disclosed herein comprises a chromium-substituted copper ferrite of formula (I) which is at least one selected from the group consisting of $CuCr_{0.2}Fe_{1.8}O_4$, $CuCr_{0.4}Fe_{1.6}O_4$, $CuCr_{0.6}Fe_{1.4}O_4$, $CuCr_{0.8}Fe_{1.2}O_4$, and $CuCrFeO_4$. Atomic ratios of the chromium-substituted copper ferrites may be determined by elemental analysis techniques such as energy-dispersive X-ray spectroscopy (EDX), X-ray photoelectron spectroscopy (XPS), inductively coupled plasma mass spectrometry (ICP-MS), and neutron activation analysis. In at least one embodiment, the spinel ferrite disclosed herein consists essentially of the chromium-substituted copper ferrite of formula (I) (i.e. oxygen atoms and metal atoms including copper, chromium, and iron), and is devoid of other metal atoms such as zinc, nickel, cobalt, aluminum, and manganese.

A particle is defined as a small object that behaves as a whole unit with respect to its transport and properties. The spinel ferrite of the present disclosure in any of its embodiments may be in the form of particles of the same shape or different shapes, and of the same size or different sizes. An average diameter (e.g., average particle size) of the particle, as used herein, refers to the average linear distance measured from one point on the particle through the center of the particle to a point directly across from it. Microparticles are particles having an average diameter between 0.1 and 100 μm in size. Nanoparticles are particles having an average diameter between 1 and 100 nm in size.

In one or more embodiments, the spinel ferrite disclosed herein is in the form of nanoparticles. The exceptionally high surface area to volume ratio of nanoparticles may cause the nanoparticles to exhibit significantly different or even novel properties from those observed in individual atoms/molecules, fine particles and/or bulk materials. In a preferred embodiment, the spinel ferrite described herein is in the form of nanoparticles, which are spherical or substantially spherical (e.g. oval, oblong, etc.) in shape. In another preferred embodiment, the spinel ferrite described herein is in the form of nanoparticles, which are angular shaped (e.g. rectangles, triangles, pentagons, prisms, prismoids, etc.). Alternatively, it is envisaged that the spinel ferrite nanoparticles may have an irregular shape. However, the spinel ferrite nanoparticles described herein may have various shapes other than spherical or angular shape and may be of any shape that provides desired antimicrobial activity. For example, the spinel ferrite nanoparticles of the present disclosure may demonstrate a variety of morphologies including, but not limited to, nanosheets, nanoplatelets, nanocrystals, nanospheres, nanohexagons, nanodisks, nanocubes, nanowires, nanofibers, nanoribbons, nanorods, nanotubes, nanocylinders, nanogranules, nanowhiskers, nanoflakes, nanofoils, nanopowders, nanoboxes, nanostars, tetrapods, nanobelts, nanaourchins, nanofloweres, and mixtures thereof.

In one or more embodiments, the spinel ferrite nanoparticles have an average particle size in a range of 20-99 nm, 25-95 nm, 30-90 nm, 35-85 nm, 40-80 nm, 45-75 nm, 50-70 nm, or SS-65 nm. However, in certain embodiments, the spinel ferrite disclosed herein has an average particle size smaller than 20 nm or greater than 99 nm. For example, the spinel ferrite disclosed herein may be in the form of microparticles having an average particle size of 0.1-100 μm, 0.5-90 μm, 1-80 μm, 5-70 μm, 10-60 μm, 20-50 μm, or 30-40 μm. In one embodiment, the spinel ferrite nanoparticles may be clustered together as agglomerates having an average diameter in a range of 0.1-5 μm, 0.2-4 μm, 0.4-2 μm, or 0.5-1 μm. In a preferred embodiment, the spinel ferrite nanoparticles are well separated from one another and do not form agglomerates. The size and shape of particles may be analyzed by techniques such as dynamic light scattering (DLS), scanning electron microscopy (SEM), transmission electron microscopy (TEM), and/or atomic force microscopy (AFM).

As used herein, "dispersity" is a measure of the heterogeneity of sizes of molecules or particles in a mixture. In probability theory or statistics, the coefficient of variation (CV), also known as relative standard deviation (RSD) is a standardized measure of dispersion of a probability distribution. It is expressed as a percentage and may be defined as the ratio of the standard deviation ($\sigma$) to the mean ($\mu$, or its absolute value $|\mu|$). The coefficient of variation or relative standard deviation is widely used to express precision and/or repeatability. It may show the extent of variability in relation to the mean of a population. In a preferred embodiment, the spinel ferrite nanoparticles of the present disclosure have a narrow size dispersion, i.e. are monodisperse. As used herein, "monodisperse", "monodispersed", and/or "monodispersity" refers to spinel ferrite nanoparticles which have a CV or RSD of less than 30%, preferably less than 25%, preferably less than 20%, preferably less than 15%, preferably less than 12%, preferably less than 10%, preferably less than 8%, preferably less than 5%.

In one or more embodiments, the spinel ferrite nanoparticles are porous. The term "microporous" means the pores of the particles have an average pore size of less than 2 nm. The term "mesoporous" means the pores of the particles have an average pore size of 2-50 nm. The term "macroporous" means the pores of the particles have an average pore size larger than 50 nm. Pore size may be determined by methods including, but not limited to, gas adsorption (e.g. $N_2$ adsorption), mercury intrusion porosimetry, and imaging techniques such as scanning electron microscopy (SEM), and x-ray computed tomography (XRCT). The spinel ferrite nanoparticles may be mesoporous, or microporous. In one embodiment, the spinel ferrite nanoparticles are microporous, and have an average pore size in a range of 0.05-1.99 nm, 0.1-1.9 nm, 0.2-1.8 nm, 0.3-1.7 nm, 0.4-1.6 nm, 0.5-1.5 nm, 0.6-1.4 nm, 0.7-1.3 nm, 0.8-1.2 nm, or 0.9-1.1 nm. In another embodiment, the spinel ferrite nanoparticles are mesoporous, and have an average pore size in a range of 2-15 nm, 3-14 nm, 4-13 nm, 5-12 nm, 6-11 nm, 7-10 nm, or 8-9 nm. In a preferred embodiment, the spinel ferrite nanoparticles comprising the chromium-substituted copper ferrite in any of their embodiments have an average pore size that is at least 1.5 mm greater than the average pore size of substantially similar spinel ferrite nanoparticles comprising a copper ferrite lacking chromium substitution (e.g. $CuFe_2O_4$), preferably at least 2 nm greater, preferably at least 3 nm greater, preferably at least 4 nm greater, preferably at least 5 nm greater, preferably at least 6 nm greater, preferably at least 7 nm greater, preferably at least 8 nm greater than the average pore size of substantially similar spinel ferrite nanoparticles comprising a copper ferrite lacking chromium substitution (see Table 2).

The Brunauer-Emmet-Teller (BET) theory (S. Brunauer, P. H. Emmett, E. Teller, J. Am. Chem. Soc. 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, pore volume and BET surface area are measured by gas adsorption analysis, preferably Na adsorption analysis. In one or more embodiments, the spinel ferrite nanoparticles of the present disclosure have a BET surface area in a range of 2-50 $m^2/g$, preferably 4-40 $m^2/g$, preferably 8-30 $m^2/g$, preferably 10-25 $m^2/g$, preferably 11-20 $m^2/g$, preferably 12-19 $m^2/g$, preferably 13-18 $m^2/g$, preferably 14-17 $m^2/g$, preferably 15-16 $m^2/g$. In one embodiment, the spinel ferrite nanoparticles, comprising the chromium-substituted copper ferrite of formula $CuCr_xFe_{2-x}O_4$, have a smaller BET surface area when the chromium content is higher (i.e. surface area decreases as "x" increases from 0.2 to 1) (see Table 2). In a preferred embodiment, the spinel ferrite nanoparticles comprising the chromium-substituted copper ferrite in any of their embodiments have a BET surface area that is at least 0.5 $m^2/g$ smaller than the average pore size of substantially similar spinel ferrite nanoparticles comprising a copper ferrite lacking chromium substitution (e.g. $CuFe_2O_4$), preferably at least 1 $m^2/g$ smaller, preferably at least 2 $m^2/g$ smaller, preferably at least 3 $m^2/g$ smaller, preferably at least 4 $m^2/g$ smaller, preferably at least 5 $m^2/g$ smaller, preferably at least 6 $m^2/g$ smaller, preferably at least 7 $m^2/g$ smaller, preferably at least 8 $m^2/g$ smaller, preferably at least 9 $m^2/g$ smaller, preferably at least 10 $m^2/g$ smaller than the BET surface area of substantially similar spinel ferrite nanoparticles comprising a copper ferrite lacking chromium substitution (e.g. $CuFe_2O_4$) (see Table 2).

As used herein, band gap energy, band gap, and/or energy gap refers to an energy range in a solid where no electron states can exist. In graphs of the electronic band structure of solids, the band gap generally refers to the energy difference (in electron volts) between the top of the valence band and the bottom of the conduction band in insulators and/or semiconductors. It is generally the energy required to promote a valence electron bound to an atom to become a conduction electron, which is free to move within the crystal lattice and serve as a charge carrier to conduct electric current. Band gap energies for the spinel ferrite nanoparticles described herein may be obtained using optical spectroscopies, e.g. UV-vis spectroscopy and/or electrochemical measurements, e.g. cyclic voltammetry (CV) and differential pulse voltammetry (DPV). In one or more embodiments, the spinel ferrite nanoparticles described herein in any of their embodiments have a band gap energy of 1.0-2.5 eV, 1.1-2.0 eV, 1.2-1.9 eV, 1.3-1.8 eV, 1.4-1.7 eV, or 1.5-1.6 eV. In certain embodiments, the spinel ferrite nanoparticles have a band gap energy smaller than 1.0 eV or greater than 2.5 eV.

As used herein, "crystallite size", "crystalline size" and/or "crystal size" refers to a Scherrer derived particle size or crystal size. A Scherrer derived particle size or crystal size relates the mean (volume average) crystal or particle size of a powder to the broadening of its powder diffraction peaks. Crystallite size is different than the aforementioned particle size as a particle may be made up of several individual crystallites. The spinel ferrite nanoparticles may be crystalline, polycrystalline, or amorphous. Preferably, the spinel ferrite nanoparticles are crystalline. In a preferred embodiment, the spinel ferrite nanoparticles of the present disclosure in any of their embodiments have an average crystallite size of 15-45 nm, preferably 18-40 nm, preferably 20-38 nm, preferably 23-35 nm, preferably 25-32 nm, preferably 28-30 nm. Crystallite size of the spinel ferrite nanoparticles may be determined via X-ray diffraction (XRD) technique. In a preferred embodiment, the spinel ferrite nanoparticles comprising the chromium-substituted copper ferrite in any of their embodiments have an average crystallite size that is at least 6 nm smaller than the average crystallite size of substantially similar spinel ferrite nanoparticles comprising a copper ferrite lacking chromium substitution (e.g. $CuFe_2O_4$), preferably at least 9 nm smaller, preferably at least 12 nm smaller, preferably at least 15 nm smaller, preferably at least 18 nm smaller, preferably at least 20 nm smaller, preferably at least 23 nm smaller, preferably at least 25 nm smaller, preferably at least 30 nm smaller than the average crystallite size of substantially similar spinel ferrite nanoparticles comprising a copper ferrite lacking chromium substitution (e.g. $CuFe_2O_4$) (see Table 1).

The method of producing the spinel ferrite nanoparticles involves mixing a copper(II) salt, a chromium(III) salt, an iron(III) salt, an inorganic base, and water to form a mixture. The water may be tap water, distilled water, bidistilled water, deionized water, deionized distilled water, reverse osmosis water, and/or some other water. In one embodiment, the water is bidistilled to eliminate trace metals. Preferably the water is distilled water. In certain embodiments, other solvents including, but not limited to, alcohols (e.g. methanol, ethanol, n-propanol, i-propanol, n-butanol), and acetone may be used in addition to or in lieu of water.

Prior to the mixing step, the aforementioned reagents (i.e. copper(II), chromium(III), and iron(III) salts, and the inorganic base) may be dissolved in water separately to form respective solutions, which are then mixed to form the mixture. In an alternative embodiment, the metal salts (i.e. copper(II), chromium(III), and iron(III) salts) are dissolved in water to form a first mixture, and an aqueous solution of the inorganic base is mixed with the first mixture to form the mixture. The mixing may occur via stirring, shaking, sonicating, blending, or by otherwise agitating the mixture. In a preferred embodiment, the mixture is stirred at a temperature of 50-95° C., 60-90° C., or 70-80° C. for 0.1-6 hours, 0.25-3 hours, or 0.5-2 hours. The stirring may by performed by a magnetic stirrer or an overhead stirrer. In another embodiment, the mixture is left to stand (i.e. not stirred). An external heat source, such as a water bath or an oil bath, an oven, or a heating mantle, may be employed to heat the mixture.

In one or more embodiments, a molar ratio of the copper (II) salt to a total mole of the chromium(III) salt and the iron(III) salt is in a range of 1:1 to 1:4, preferably 2:3 to 1:3, more preferably 1:1.8 to 2:5, or about 1:2. Based on the aforementioned chromium-substituted copper ferrite of formula $CuCr_xFe_{2-x}O_4$, a molar ratio of the chromium(III) salt to the iron(III) salt may be represented as a ratio of "x" to "2-x". For example, a molar ratio of the chromium(III) salt to the iron(III) salt may be about 1:19 for the preparation of spinel ferrite nanoparticles comprising chromium-substituted copper ferrite of formula $CuCr_{0.1}Fe_{1.9}O_4$. A molar ratio of the chromium(III) salt to the iron(III) salt may be about 1:1 for the preparation of spinel ferrite nanoparticles comprising chromium-substituted copper ferrite of formula $CuCrFeO_4$. In one embodiment, an overall concentration of the copper(II) salt, the chromium(III) salt and the iron(III) salt in the mixture may be in the range of 0.01-50 M, 0.05-40 M, 0.1-30 M, 0.5-15 M, 1-10 M, 2-6 M, or 3-4 M.

Non-limiting examples of the copper(II) salt include copper(II) nitrate, copper(II) chloride, copper(II) sulfate, copper(II) bromide, copper(II) iodide, and mixtures thereof. The copper(II) salt used herein may be in any hydration state, for instance, copper(II) nitrate includes, without limitation, $Cu(NO_3)_2$, $Cu(NO_3)_2 \cdot H_2O$, $Cu(NO_3)_2 \cdot 2.5H_2O$, $Cu(NO_3)_2 \cdot 3H_2O$, and $Cu(NO_3)_2 \cdot 6H_2O$. In certain embodiments, a copper salt having a different oxidation state, such as +1, may be used in addition to or in lieu of the copper(II) salt. In a preferred embodiment, the copper(II) salt is copper (II) nitrate.

Non-limiting examples of the chromium(III) salt include chromium(III) chloride, chromium(III) nitrate, chromium (III) sulfate, chromium(III) bromide, chromium(III) fluoride, and mixtures thereof. The chromium(III) salt used herein may be in any hydration state, for example, chromium(III) chloride includes, but are not limited to, $CrCl_3$, $CrCl_3 \cdot 5H_2O$, and $CrCl_31 \cdot 6H_2O$. In certain embodiments, a chromium salt having a different oxidation state, such as +2, may be used in addition to or in lieu of the chromium(III) salt. In a preferred embodiment, the chromium(III) salt is chromium(III) chloride.

Non-limiting examples of the iron(III) salt include iron (III) nitrate, iron(III) chloride, iron(III) sulfate, iron(III) bromide, iron(III) fluoride, iron(III) phosphate, and mixtures thereof. The iron(III) salt used herein may be in any hydration state, for instance, iron(III) nitrate includes, without limitation, $Fe(NO_3)_3$, $Fe(NO_3)_3 \cdot 6H_2O$, and $Fe(NO_3)_3 \cdot 9H_2O$. In certain embodiments, an iron salt having a different oxidation state, such as +2, may be used in addition to or in lieu of the iron(III) salt. In a preferred embodiment, the iron(III) salt is iron(III) nitrate.

In one embodiment, the inorganic base is sodium hydroxide (NaOH), potassium hydroxide (KOH), ammonium hydroxide ($NH_4OH$), cesium hydroxide (CsOH), lithium hydroxide (LiOH), calcium hydroxide ($Ca(OH)_2$), barium hydroxide ($Ba(OH)_2$), strontium hydroxide ($Sr(OH)_2$), sodium carbonate ($Na_2CO_3$), potassium carbonate ($K_2CO_3$), cesium carbonate ($Cs_2CO_3$), trisodium phosphate ($Na_3PO_4$), or a mixture thereof. In a preferred embodiment. the inorganic base is sodium hydroxide. In a preferred embodiment, the pH of the mixture is maintained at a range of 9-13, preferably 9.5-12.5, preferably 10-12, preferably 10.5-11.5, or about 11. The pH of the mixture may be monitored using a pH meter, pH test papers, and/or pH indicators.

The method also involves the step of heating the mixture to form a precipitate. In a preferred embodiment, the mixture is heated at a first temperature of 40-100° C., preferably 50-90° C., preferably 60-85° C., preferably 70-80° C. for 0.1-3 hours, 0.25-2 hours, 0.5-1 hour, or about 40 minutes, and subsequently at a second temperature of 110-180° C., preferably 120-170° C., preferably 130-160° C., preferably 140-150° C. for 1-6 hours, 2-5 hours, 2.5-4 hours, or about 3 hours. A precipitation may be formed during the heating processes and be separated (e.g. filtered off, centrifuged) from the aforementioned mixture. Alternatively, the mixture may be heated in a single stage. For example, the mixture may be heated at a temperature of 40-180° C., preferably 60-160° C., more preferably 80-130° C. for 0.5-12 hours, 1-6 hours, or 2-4 hours.

The method further involves the step of drying the precipitate at a temperature of 40-600° C., 60-500° C., 80-400° C., 100-300° C., or 150-250° C. for 1-48 hours, 2-36 hours, 4-24 hours, or 8-12 hours to produce the spinel ferrite nanoparticles. In one embodiment, this step involves an initial heating of the precipitate at a temperature of 40-150° C., preferably 50-120° C., more preferably 60-90° C., or about 70° C. for 1-36 hours, 2-24 hours, 4-12 hours, or about 6 hours, and an additional heat treatment (i.e. annealing) of the precipitate at a temperature of 200-600° C., preferably 300-500° C., more preferably 350-450° C., or about 400° C. for 1-24 hours, 2-12 hours, 3-6 hours, or about 4 hours. In a related embodiment, the initial heating may be performed using a hot plate, an oven, or in some embodiments, the precipitate may be subjected to a vacuum, or a rotary evaporator. In another related embodiment, the additional heat treatment (i.e. annealing) may be conducted in air within an oven or furnace. Also, in some embodiments, the precipitate may not be annealed via additional heating in air, but in oxygen-enriched air, an inert gas, or a vacuum.

In at least one embodiment, the currently disclosed method in any of its embodiments does not involve the usage of chelating agent such as urea, thiourea, citric acid, ethylenediaminetetraacetic acid (EDTA), oxalic acid, malic acid, sebacic acid, tartaric acid, glucose, amino acids such as glutamine and histidine, as well as other triprotic acids such as isocitric acid, aconitic acid, and propane-1,2,3-tricarboxylic acid, which are commonly applied in sol-gel auto-combustion technique for the production of spinel nanoparticles.

A further aspect of the present disclosure relates to spinel ferrite nanoparticles, comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$. In one embodiment, the spinel ferrite nanoparticles comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$ are made by the method of the first aspect of the current disclosure. Thus, the spinel ferrite nanoparticles may have similar properties as described for those in the first aspect, such as average particle size, surface area, pore size, crystallite size, and/or some other property. Preferably, the spinel ferrite nanoparticles of the current aspect have aforementioned composition ratios, shapes, average particle sizes, BET surface areas, average pore sizes, and average crystallite sizes. In one embodiment, these spinel ferrite nanoparticles may have an average particle size in a range of 20-80 nm, 25-75 nm, 30-70 nm, 35-65 nm, 40-60 nm, or 45-55 nm. In another embodiment, these spinel ferrite nanoparticles have an average pore size in a range of 5-20 nm, 6-19 nm, 7-18 nm, 8-17 nm, 9-16 nm, 10-15 nm, 11-14 nm, or 12-13 nm. In another embodiment, these spinel ferrite nanoparticles have a BET surface area in a range of 5-18 $m^2/g$, preferably 6-17 $m^2/g$, preferably 7-16 $m^2/g$, preferably 8-15 $m^2/g$, preferably 9-14 $m^2/g$, preferably 10-13 $m^2/g$, preferably 11-12 $m^2/g$. In another embodiment, these spinel ferrite nanoparticles have an average crystallite size in a range of 15-40 nm, preferably 18-38 nm, preferably 20-35 nm, preferably 23-32 nm, preferably 25-30 μm, preferably 26-28 nm. Alternatively, the spinel ferrite nanoparticles comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$ may be prepared by other applicable processes including, but not limited to, sol-gel method, sol-gel auto-combustion, sonochemical method, ball milling, hydrothermal process, solvothermal process, aerosol spray pyrolysis method, and biological approach.

According to a second aspect, the present disclosure relates to a method for preventing or reducing growth of a microorganism on a surface using spinel ferrite nanoparticles comprising chromium-substituted copper ferrite of formula $CuCr_xFe_{2-x}O_4$, wherein x is greater than 0 and smaller than 2, preferably x is in a range of $0<x \leq 1.5$, more preferably x is in a range of $0.1 \leq x \leq 1.0$. In one or more embodiments, the spinel ferrite used herein comprises a chromium-substituted copper ferrite which is at least one selected from the group consisting of $CuCr_{0.2}Fe_{1.8}O_4$, $CuCr_{0.4}Fe_{1.6}O_4$, $CuCr_{0.6}Fe_{1.4}O_4$, $CuCr_{0.8}Fe_{1.2}O_4$, and $CuCrFeO_4$, Preferably, these spinel ferrite nanoparticles may have an average particle size in a range of 20-99 nm, 25-95 nm, 30-90 nm, 35-85 nm, 40-80 nm, 45-75 nm, 50-70 nm, or 55-65 nm. The spinel ferrite nanoparticles may have similar properties as described for those in the first aspect, such as average particle size, surface area, pore size, crystallite size, and/or some other property. In preferred embodiments, the spinel ferrite nanoparticles used herein for preventing or reducing growth of a microorganism on a surface have aforementioned composition ratios, shapes, average particle sizes, BET surface areas, average pore sizes, and average crystallite sizes.

In other embodiments, the spinel ferrite nanoparticles having one or more dissimilar properties as compared to those described in the first aspect may be used herein for preventing or reducing growth of a microorganism on a surface. For example, spinel ferrite nanoparticles may be used which have an average particle size smaller than 20 nm or greater than 99 nm. Alternatively, spinel ferrite nanoparticles may be used which have a BET surface area smaller than 2 $m^2/g$ or greater than 50 $m^2/g$, and/or an average crystallite size smaller than 15 nm or greater than 45 nm. In a related embodiment, spinel ferrite nanoparticles which are microporous, mesoporous, or macroporous may be used herein for preventing or reducing growth of a microorganism on a surface, or in some embodiments, spinel ferrite nanoparticles which are dense (i.e. non-porous) may be used instead. These spinel ferrite nanoparticles with dissimilar properties may be formed by changing the aforementioned reaction conditions, such as solvent, reaction time, pH, and/or temperature. Alternatively, these spinel ferrite nanoparticles with dissimilar properties may be prepared via different synthetic routes such as sol-gel auto-combustion, microwave-assisted method, solid-state reaction, and hydrothermal synthesis.

The current method for preventing or reducing growth of a microorganism on a surface involves applying the spinel ferrite nanoparticles onto the surface. Preferably, the spinel ferrite nanoparticles are in contact with the surface for 0.1-48 hours, 0.5-36 hours, 1-24 hours, 2-12 hours, or 3-6 hours.

In one or more embodiments, the spinel ferrite nanoparticles are applied onto the surface as a mixture (e.g. a suspension, a solution, a colloid) comprising the spinel ferrite nanoparticles. Preferably, the spinel ferrite nanoparticles are applied onto the surface as a suspension comprising a solvent and the spinel ferrite nanoparticles. The suspension may comprise 10 μg/mL to 1,000 mg/mL of the spinel ferrite nanoparticles relative to a total volume of the suspension, preferably 50 μg/mL to 800 mg/mL, preferably 100 μg/mL to 600 mg/mL, preferably 500 μg/mL to 400 mg/mL, preferably 1 to 200 mg/mL, preferably 2.5 to 150 mg/mL, preferably 4 to 125 mg/mL, preferably 8 to 100 mg/mL, preferably 16 to 90 mg/mL, preferably 32 to 80 mg/mL, preferably 40 to 70 mg/mL, preferably 50 to 60 mg/mL. In one or more embodiments, the spinel ferrite nanoparticles used herein comprise a chromium-substituted copper ferrite which is at least one selected from the group consisting of $CuCr_{0.2}Fe_{1.8}O_4$, $CuCr_{0.4}Fe_{1.6}O_4$, $CuCr_{0.6}Fe_{1.4}O_4$, $CuCr_{0.8}Fe_{1.2}O_4$, and $CuCrFeO_4$. In a preferred embodiment, the spinel ferrite nanoparticles used herein comprise a chromium-substituted copper ferrite which is at least one selected from the group consisting of $CuCr_{0.4}Fe_{1.6}O_4$, $CuCr_{0.8}Fe_{1.2}O_4$, and $CuCrFeO_4$. In one or more embodiments, the solvent comprises water. In a related embodiment, other compatible solvents, such as phosphate-buffered saline, alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), acetonitrile, and dimethyl sulfoxide (DMSO), may be used in addition to or in lieu of water. Alternatively, the solvent may be chlorinated solvents (e.g. chlorobenzene, dichloromethane, 1,2-dichloroethane, 1,1-dichloroethane, chloroform), ester solvents (e.g. ethyl acetate, propyl acetate), ethers (e.g. diethyl ether, tetrahydrofuran, 1,4-dioxane, tetrahydropyran, t-butyl methyl ether, cyclopentyl methyl ether, di-iso-propyl ether), aromatic solvents (e.g. benzene, o-xylene, m-xylene, p-xylene, mixtures of xylenes, toluene, mesitylene, anisole, 1,2-dimethoxybenzene, $\alpha,\alpha,\alpha$-trifluoromethylbenzene, fluorobenzene), or a mixture thereof.

As used herein, "microorganism" or "microbe" refers to in particular fungi, and gram-positive and gram-negative bacteria. The term "antimicrobial product" refers to a product demonstrating the capability to inhibit or prevent the proliferation of microorganisms. Gram-negative bacteria are bacteria that do not retain the crystal violet stain used in the gram-staining method of bacterial differentiation. Gram-negative bacteria are considered great medical challenges as the thick outer membrane protects these bacteria from many antibiotics, dyes, and detergents.

In one or more embodiments, the spinel ferrite nanoparticles are applied onto the surface as an antimicrobial product containing the spinel ferrite nanoparticles at an amount of 0.01-99 wt %, 0.5-95 wt %, 1-90 wt %, 2-80 wt %, 5-70 wt %, 10-60 wt %, 20-50 wt %, 30-40 wt % relative to a total weight of the antibacterial product. In one or more embodiments, the spinel ferrite nanoparticles used herein comprise a chromium-substituted copper ferrite which is at least one selected from the group consisting of $CuCr_{0.2}Fe_{1.8}O_4$, $CuCr_{0.4}Fe_{1.6}O_4$, $CuCr_{0.6}Fe_{1.4}O_4$, $CuCr_{0.8}Fe_{1.2}O_4$, and $CuCrFeO_4$. In a preferred embodiment, the spinel ferrite nanoparticles used herein comprise a chromium-substituted copper ferrite which is at least one selected from the group consisting of $CuCr_{0.4}Fe_{1.6}O_4$, $CuCr_{0.8}Fe_{1.2}O_4$, and $CuCrFeO_4$.

Exemplary antimicrobial products include, but are not limited to, antimicrobial coatings, hand sanitizer (including rinse off and leave-on and aqueous-based hand disinfectants), preoperative skin disinfectant, bar soap, liquid soap (e.g., hand soap), hospital disinfectants, disinfecting spray solution, household cleansing wipes, surface sanitizer, personal care disinfecting wipes, body wash, acne treatment products, antibacterial diaper rash cream, antibacterial skin cream, deodorant, antimicrobial creams, topical cream, a wound care item, such as wound healing ointments, creams, and lotions.

The method disclosed herein may be used to prevent or reduce growth of a microorganism on the skin of a subject. In a preferred embodiment, the spinel ferrite nanoparticles are applied onto the skin of a subject as an antimicrobial cream comprising 0.01-50 wt %, 0.1-40 wt %, 1-30 wt %, 2-20 wt %, 4-15 wt %, or 5-10 wt % of spinel ferrite nanoparticles relative to a total weight of the antimicrobial cream. The subject may be a mammal, such as a human; a non-human primate, such as a chimpanzee, and other apes and monkey species; a farm animal, such as a cow, a horse, a sheep, a goat, and a pig; a domestic animal, such as a rabbit, a dog, and a cat; a laboratory animal including a rodent, such as a rat, a mouse, and a guinea pig, and the like. The antimicrobial cream may further comprise other formulating components such as occlusion components (e.g. petrolatum), film forming agents (e.g. polyvinylpyrrolidone), thickening agents (e.g. xanthan gum, polyacrylamide polymers), and/or emulsifiers (e.g. fatty acids, fatty alcohols).

The formulation techniques of topical creams are generally known to those skilled in the art.

Other surfaces suitable for the method disclosed herein include both hard and soft surfaces. The term "hard surface" includes, but is not limited to, bathroom surfaces (tub and tile, fixtures, ceramics), kitchen surfaces, countertops, appliances, flooring, glass, automobiles, and the like. "Soft surfaces" include but are not limited to fabrics, leather, carpets, furniture, upholstery and other suitable soft surfaces. The presently disclosed method may also be viable for sanitizing surfaces related to hospital and nursing care facilities and equipment such as hospital room, toilet, beds, sheets, pillows, wheelchairs, and canes.

The method disclosed herein may also be used to prevent or reduce growth of a microorganism on the surface of an artificial restoration or medical device. Exemplary artificial restorations include, without limitation, dental restorations, dentures, dental prosthesis, craniofacial implants, artificial joints, and artificial bones. Exemplary medical devices include, but are not limited to, catheters, medical diagnosis instruments such as endoscopes, contact lenses, spectacles, hearing aids, and mouth guards.

The spinel ferrite nanoparticles may be applied onto a desired area of the surface as needed. In certain embodiments, the method disclosed herein involves applying the spinel ferrite nanoparticles onto the surface 1 to 10 times daily, preferably 2 to 7 times daily, preferably 3 to 5 times daily. In some embodiments, the interval of time between each application of the spinel ferrite nanoparticles may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between.

In one embodiment, the aforementioned method in any of its embodiments may prevent or reduce growth of gram-negative bacteria including, but not limited to, *Escherichia coli, Escherichia fergusonii, Escherichia hermannii, Escherichia vulneris, Shigella boydii, Shigella dysenteriae, Shigella flexneri, Shigella sonnei, Proteus mirabilis, Proteus penneri, Proteus vulgaris, Cronobacter sakazakii, Pantoea agglomerans, Serratia marcescens, Citrobacter amalonaticus, Citrobacter braakii, Citrobacter freundii, Citrobacter koseri, Klebsiella granulomatis, Klebsiella oxytoca, Klebsiella pneumoniae, Klebsiella variicola, Acinetobacter baumannii, Acinetobacter calcoaceticus, Acinetobacter colistiniresistens, Acinetobacter defluvii, Acinetobacter haemolyticus, Acinetobacter junii, Acinetobacter lwoffii, Acinetobacter pittii, Acinetobacter schindleri, Acinetobacter soli, Enterobacter aerogenes, Enterobacter taylorae, Pseudomonas aeruginosa, Neisseria meningitidis, Neisseria gonorrhoeae, Pseudomonas pseudomallei, Treponema pallidum, Mycobacterium tuberculosis, Salmonella* spec., alpha-Proteobacteria (particularly *Agrobacterium* spec.), beta-Proteobacteria (particularly *Nitrosomonas* spec.), *Aquabacterium* spec., Gammaproteobacteria, *Stenotrophomonas* spec. (particularly *S. maltophilia*), *Xanthomonas* spec. (*X. campestris*), *Neisseria* spec., and *Haemophilus* spec. Pathogenic strains of *Escherichia coli* (*E. coli*) can cause gastroenteritis, urinary tract infections, neonatal meningitis, hemorrhagic colitis, and Crohn's disease. Common signs and symptoms include severe abdominal cramps, diarrhea, hemorrhagic colitis, vomiting, and sometimes fever. In at least one embodiment, the method disclosed herein in any of its embodiments may prevent or reduce growth of *E. coli*.

The method disclosed herein in any of its embodiments may be effective on pathogenic gram-positive bacteria including, but not limited to, *Staphylococcus aureus*, MRSA, *Staphylococcus auricularis, Staphylococcus capitis, Staphylococcus caprae, Staphylococcus cohnii, Staphylococcus delphini, Staphylococcus epidermis, Staphylococcus felis, Staphylococcus gallinarum, Staphylococcus haemolyticus, Staphylococcus hominis, Staphylococcus hyicus, Staphylococcus lugdunensis, Staphylococcus pettenkoferi, Staphylococcus pseudintermedius, Staphylococcus rostri, Staphylococcus saccharolyticus, Staphylococcus saprophyticus, Staphylococcus schleiferi, Staphylococcus vitulinus, Staphylococcus warneri, Staphylococcus xylosus, Streptococcus pyogenes, Corynebacterium* spp. (particularly *C. tenuis, C. diphtheriae*, and *C. minutissimum*), *Micrococcus* spp. (particularly *M. sedentarius*), *Bacillus anthracis, Streptococcus* spec. (particularly *S. gordonii*, and *S. mutans*), *Actinomyces* spec. (particularly *A. naeslundii*), and *Actinobacteria* (particularly *Brachybacterium* spec.).

In certain embodiments, preventing or reducing growth of a microorganism on the surface may be evaluated by measuring microbial counts of the surface before and/or at least 30 minutes, preferably at least 1 hour, more preferably at least 2 hours after applying the surface with the spinel ferrite nanoparticles via the method described herein in any of its embodiments. For example, the number of viable microorganisms is counted using a slide count method and/or a direct culture method (plate count).

The "slide count" method utilizes a microscope slide in a chamber that is especially designed to enable cell counting. A total number of cells in a sample can be determined by looking at the sample under a microscope and counting the number manually. A number of viable cells can also be determined using the slide count method if a viability dye is added to the sample. Exemplary viability dyes include, but are not limited to, Trypan Blue, Calcein-AM, Erythrosine B, propidium iodide, and 7-aminoactinomycin D.

"Colony-forming unit (CFU)" refers to a unit used to estimate the number of viable bacteria or fungal cells in a sample. The purpose of direct culture method (plate count) is to estimate the number of cells present based on their ability to give rise to colonies under specific conditions of nutrient medium, temperature and time. Theoretically, one viable cell can give rise to a colony through replication. A sample solution of microbes at an unknown concentration is often serially diluted in order to obtain at least one plate with a countable number of CFUs. Counting colonies is performed manually using a pen and a click-counter, or automatically using an automated system and a software tool for counting CFUs.

Preventing or reducing growth of a microorganism on a surface may be understood to indicate a reduction of the number of microorganism cells on the surface after applying the spinel ferrite nanoparticles onto the surface. In some embodiments, the number of microorganisms on the surface characterized by a microbial count is reduced by at least 10%, preferably at least 20%, more preferably at least 30%, more preferably at least 40%, more preferably at least 45%, more preferably at least 50%, more preferably at least 55%, more preferably at least 60%, more preferably at least 65%, more preferably at least 70%, more preferably at least 80%, more preferably at least 90%, or more preferably at least 95%, with respect to use of an untreated control surface.

Ideally, the growth of microorganisms on the surface may be completely or almost completely prevented.

As defined herein, the minimum inhibitory concentration (MIC) of an antimicrobial composition for a given microorganism is the lowest concentration of the composition required to inhibit the growth of the microorganism. The minimum bactericidal concentration (MBC) is the lowest concentration of the antimicrobial composition required to kill the microorganism. In general, an antimicrobial composition is regarded as bactericidal if the MBC is no more than four times the MIC.

In one embodiment, the antimicrobial efficacy of the spinel ferrite nanoparticles comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$ is demonstrated by test data showing the minimum inhibitory concentrations (MIC) and minimum bactericidal concentrations (MBC) against microorganisms (e.g. E. coli) cultured in vitro under standard conditions (see Examples 8-13).

In a preferred embodiment, the spinel ferrite nanoparticles comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$ have a MIC against E. coli that is at least 50% smaller than the MIC against E. coli of substantially similar spinel ferrite nanoparticles comprising a copper ferrite lacking chromium substitution (e.g. $CuFe_2O_4$), preferably at least 60% smaller, preferably at least 70% smaller, preferably at least 75% smaller, preferably at least 80% smaller, preferably at least 85% smaller, preferably at least 87.5% smaller, preferably at least 90% smaller, preferably at least. 95% smaller than the MIC against E. coli of substantially similar spinel ferrite nanoparticles comprising a copper ferrite lacking chromium substitution (see Table 3). In a related embodiment, the spinel ferrite nanoparticles comprising at least one chromium-substituted copper ferrite selected from the group consisting of $CuCr_{0.4}Fe_{1.6}O_4$, $CuCr_{0.6}Fe_{1.4}O_4$, $CuCr_{0.8}Fe_{1.2}O_4$, and $CuCrFeO_4$ in any of their embodiments have a MBC against E. coli that is at least 50% smaller than the MBC against E. coli of substantially similar spinel ferrite nanoparticles comprising a copper ferrite lacking chromium substitution (e.g. $CuFe_2O_4$), preferably at least 60% smaller, preferably at least 70% smaller, preferably at least 75% smaller, preferably at least 80% smaller, preferably at least 85% smaller than the MBC against E. coli of substantially similar spinel ferrite nanoparticles comprising a copper ferrite lacking chromium substitution (see Table 3).

The examples below are intended to further illustrate protocols for preparing, characterizing spinel ferrite nanoparticles, and uses thereof, and are not intended to limit the scope of the claims.

EXAMPLE 1

Synthesis of Chromium-Substituted Copper Ferrite Nanoparticles

Chromium-substituted copper ferrite nanoparticles with a chemical composition of $CuCr_xFe_{2-x}O_4$, where x=0.0, 0.2, 0.4, 0.6, 0.8 and 1.0, were prepared by co-precipitation method using copper(II) nitrate pentahydrate $(Cu(NO_3)_2 \cdot 5H_2O)$, chromium(III) chloride hexahydrate $(CrCl_2 \cdot 6H_2O)$, iron nitrate $(Fe(NO_3)_3)$, and sodium hydroxide (NaOH) as precursor reagents. The precursor materials were dissolved in 100 ml distilled water by applying a constant stirring for 40 min at a temperature of 80° C. The pH of the reaction mixture was maintained at 11 using NaOH. The precipitation process was continued for 3 h at 130° C. and then the reaction mixture was dried by heating at 70° C. for 6 h. Finally, all the synthesized products were annealed by heating at 400° C. for 4 h.

EXAMPLE 2

Characterization Methods

The phase and crystallographic analysis of synthesized ferrite nanoparticles were carried out using CuKα radiation (λ=1.514 Å) with an XRD equipment built by Rigaku D/Max-IIIC Diffractometer (Japan). The crystalline size of each composition was calculated using Sherrer's formula [Ansari M A, Khan H M, Khan A A, Sultan A, Azam A. Synthesis and characterization of the antibacterial potential of ZnO nanoparticles against extended-spectrum β-lactamases-producing Escherichia coli and Klebsiella pneumoniae isolated from a tertiary care hospital of North India, Applied microbiology and biotechnology. 2012; 94(2):467-77]. The experimental lattice parameter (α) was calculated using the formula described by Klug et al. [Klug H P, L. E. Alexander, X-ray Diffraction Procedures For polycrystalline and Amorphous Materials, John Wiley & Sons, Inc., New York, 1954, L. Lutterotti, P. Scardi, J. Appl. Crystallogr. 1990 23:246-252].

X-ray density, apparent density, porosity, and effect of substitution of $Cr^{3+}$ hopping length between the two sublattice sites have been estimated using the formula described by Batoo et al. [Batoo K M, G. Kumar, Y. Yang, Y. Al-Douri, M. Singh, R. B. Jotania, A. Imran, J. Alloys and Compd. 2017, 726:179-186]. The spectral analysis of the samples was measured by FT-IR (Bruker) spectrophotometer. Optical properties of the samples (diffuse reflectance, DR) were conducted using a UV-Vis spectrophotometer (Evolution 300 PC Thermo Scientific) equipped with Praying Mantis Diffuse Reflectance accessory. The optical energy band gap ($E_g$) of synthesized nanoparticles was assessed by applying the Kubelka-Munk (K-M) model [Baykal A, S. Esir, A. Demir, S. Güner, Magnetic and optical properties of $Cu_{1-x}Zn_xFe_2O_4$ nanoparticles dispersed in a silica matrix by a sol-gel auto-combustion method, Ceramics International. 2015, 41:231-239; and Barathiraja C, A. Manikandan, A. M. Uduman Mohideen, S. Jayasree, S. A. Antony, Magnetically recyclable spinel $Mn_xNi_{1-x}Fe_2O_4$ (x=0.0-0.5) nano-photocatalysts: Structural, morphological and opto-magnetic properties, Journal of Superconductivity and Novel Magnetism. 2016, 29:477-486, each incorporated herein by reference in their entirety]. DR % measurements can be used to determine the absorption coefficient (α) using the formula given below:

$$F(R) \equiv \alpha = \frac{(1-R)^2}{2R}$$

where F(R) is the Kubelka-Munk function, (α) is absorption coefficient, and R is reflectance.

The morphology of the ferrite nanoparticles was examined by SEM (JEOL JSM-6490). The textural properties and nitrogen adsorption/desorption isotherms of as-prepared nanoparticles were measured using liquid nitrogen (77 K) by Micromeritics ASAP 2020 automatic analyzer. Before performing the analysis, each sample was heated at 150° C. for 3 h to eliminate unwanted gas. BET analysis was used to determine the surface area while the pore size and volume distribution data were obtained by applying BJH method.

EXAMPLE 3

X-Ray Diffraction Analysis of Synthesized CuCr$_x$Fe$_{2-x}$O$_4$ (0.0≤x≤1.0) Nanoparticles (NPs)

X-ray diffraction patterns of synthesized CuCr$_x$Fe$_{2-x}$O$_4$ (0.0≤x≤1.0) NPs were analyzed using powder-X software (FIGS. 1A-F). The most intense reflection peak (311) was observed at 34.8°, which is a characteristic peak of spinel phase. Further, the peaks (220), (311), (222), (400), (511), (440), and (531) indicate the presence of a cubic spinel phase with the space group Fd$_3$m (Samavati A, Ismail A F. Antibacterial properties of copper-substituted cobalt ferrite nanoparticles synthesized by co-precipitation method. Particuology. 2017; 30:158-63; and Ashour A H, El-Batal A I, Abdel Maksoud M I A, El-Sayyad G S, Labibc S, Abdeltwab E, El-Okr M M. Antimicrobial activity of metal-substituted cobalt ferrite nanoparticles synthesized by sol-gel technique. Particuology. 2018; volume 40, pages 141-151, each incorporated herein by reference in their entirety]. The estimated crystallite sizes obtained from the Scherer plots were ~43.3, ~25.6, ~34.5, ~27.5, 22.9, and ~20.2 nm for x=0.00, 0.2, 0.4, 0.6, 0.8, and 1, respectively (Table 1). It has been found that the crystallite size decreased linearly with increasing substitution of the dopant ion (Cr), obeying Vegard's law. The results obtained are in good agreement with those of Samavati and Ismail (2017) where they found that the crystallite size decreased with increasing Cu content in copper-substituted cobalt ferrite nanoparticles synthesized by co-precipitation method. It was also observed that the lattice parameter increased linearly as the concentration of Cr$^{3+}$ ions increased (Table 1). Both X-ray and bulk densities were found to increase slightly with the substitution of the Cr$^{3+}$ ions. The slight increase in porosity could be reasoned on the basis that the density of the Cr$^{3+}$ ion (7.19 g/cm$^3$) is less than the density of the replacing element Fe$^{3+}$ ion (7.874 g/cm$^3$), which caused decreases in X-ray as well as apparent density and an increase in porosity (Table 1). It was noted that the hopping length was affected by substitution of Cr$^{3+}$ as the hopping length increased at both A- and B-Sites slightly upon the substitution. The above observation may be resulted from the fact that Cr$^{3+}$ ions have an occupational preference for octahedral B-site, however when the concentration of Cr$^{3+}$ ions increases to a certain limit, the ions can also occupy tetrahedral A-site, as reported in the literature [Haralkar S. J., R. H. Kadam, S. S. More, Sagar E. Shirsath, S. Patil, D. R. Mane, Phys. B, Cond. Matt. 2012 407:4338-4346; and More S. S. R. H. Kadam, A. B. Kadam, A. R. Shite, D. R. Mane, K. M. Jadhav, J. Alloy. Compds. 2010, 502:477-479, each incorporated herein by reference in their entirety].

TABLE 1

Cr content and structural parameters of CuCr$_x$Fe$_{2-x}$O$_4$ (0.0 ≤ x ≤ 1.0) NPs

| Sample | Crystallite size | Lattice Parameter (a) | X-ray density ($\rho_x$) | Th. Density ($\rho$) | Porosity | Hopping Length | |
|---|---|---|---|---|---|---|---|
| x | (nm) | (Å) | (g/cm$^3$) | (g/cm$^3$) | (%) | A-Site | B-Site |
| 0 | 43.33 | 8.485 | 14.85 | 11.56 | 22.15 | 3.6525 | 2.9822 |
| 0.2 | 25.65 | 8.4856 | 14.83 | 11.42 | 22.99 | 3.6527 | 2.9824 |
| 0.4 | 34.58 | 8.4856 | 14.55 | 11.28 | 22.47 | 3.6743 | 3.0001 |

TABLE 1-continued

Cr content and structural parameters of CuCr$_x$Fe$_{2-x}$O$_4$ (0.0 ≤ x ≤ 1.0) NPs

| Sample | Crystallite size | Lattice Parameter (a) | X-ray density ($\rho_x$) | Th. Density ($\rho$) | Porosity | Hopping Length | |
|---|---|---|---|---|---|---|---|
| x | (nm) | (Å) | (g/cm$^3$) | (g/cm$^3$) | (%) | A-Site | B-Site |
| 0.6 | 27.54 | 8.4865 | 14.53 | 11.02 | 24.15 | 3.6747 | 3.0004 |
| 0.8 | 22.98 | 8.4869 | 14.5 | 10.95 | 24.68 | 3.6749 | 3.0005 |
| 1 | 20.21 | 8.4873 | 14.5 | 10.82 | 25.37 | 3.6751 | 3.0007 |

EXAMPLE 4

FT-IR Analysis of Synthesized CuCr$_x$Fe$_{2-x}$O$_4$ (0.0≤x≤1.0) NPs

Figure 2:
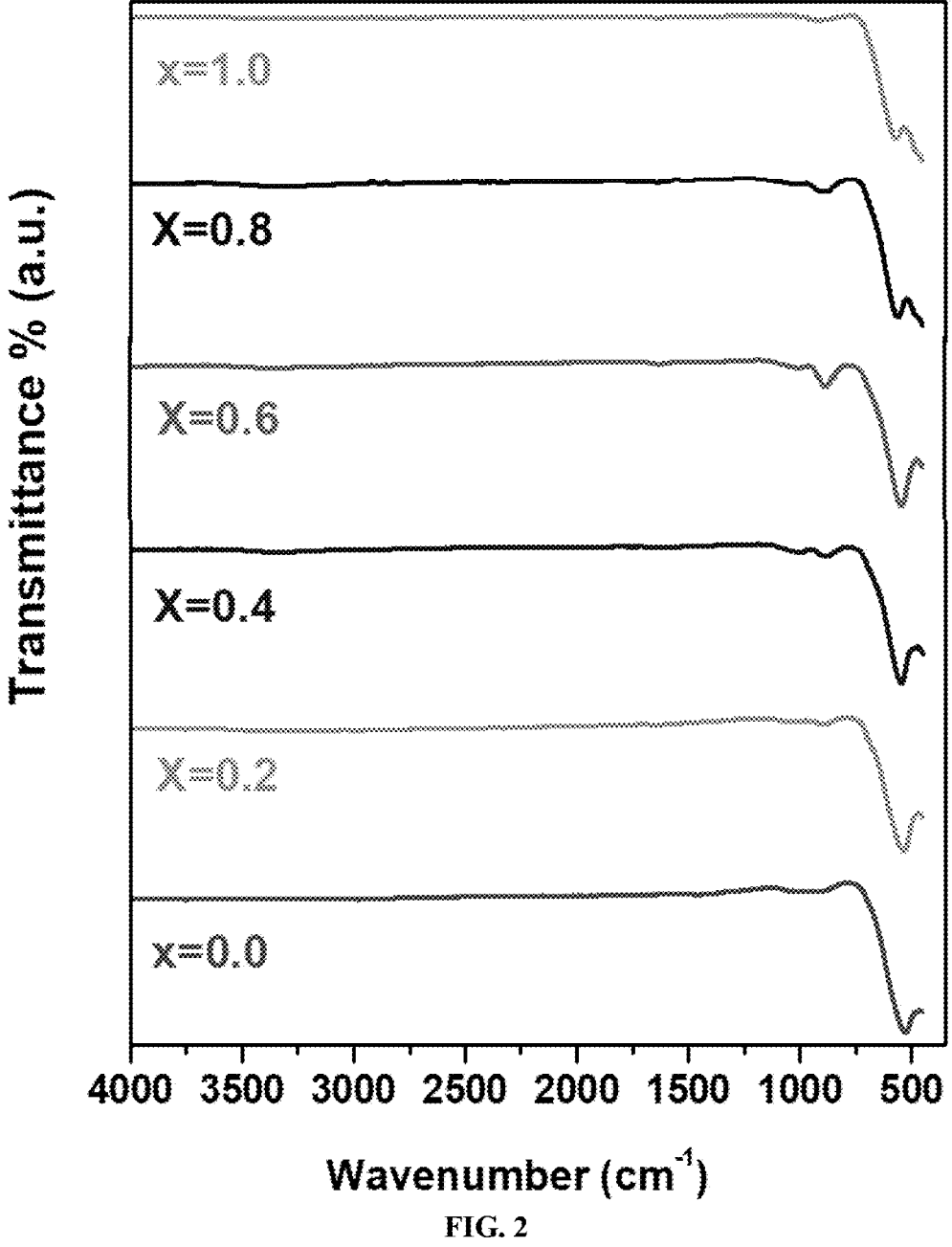
FIG. 2 is an overlay of FT-IR spectra of spinel ferrite nanoparticles containing $CuCrFeO_4$ (x=1), $CuCr_{0.8}Fe_{1.2}O_4$ (x=0.8), $CuCr_{0.6}Fe_{1.4}O_4$ (x=0.6), $CuCr_{0.4}Fe_{1.6}O_4$ (x=0.4), $CuCr_{0.2}Fe_{1.8}O_4$ (x=0.2), and $CuFe_2O_4$ (x=0.0), respectively.

FT-IR spectral analyses of synthesized spinel CuCr$_x$Fe$_{2-x}$O$_4$ (0.0≤x≤1.0) NPs recorded in the range of 400-4000 cm$^{-1}$ were shown in FIG. 2. The spinel ferrite nanoparticles often exhibit two FTIR-active bands, designated as w$_1$ (higher absorption band) and w$_2$ (lower absorption band) in the range of 450-900 cm$^{-1}$ [Padmapriya G, Manikandan A, Krishnasamy V, Jaganathan S K, Antony S A. Spinel Ni$_x$Zn$_{1-x}$Fe$_2$O$_4$ (0.0≤x≤1.0) nano-photocatalysts: synthesis, characterization and photocatalytic degradation of methylene blue dye. Journal of Molecular Structure. 2016; 1119: 39-47, incorporated herein by reference in its entirety]. In the present disclosure, FT-IR spectra of all the samples exhibit two intense peaks at ~500 cm$^{-1}$ (lower peak) and ~850 cm$^{-1}$ (higher peak) corresponding to metal oxygen (Cu—O, Cr—O, and Fe—O) bonds [Padmapriya G, Manikandan A, Krishnasamy V, Jaganathan S K, Antony S A. Spinel Ni$_x$Zn$_{1-x}$Fe$_2$O$_4$ (0.0≤x≤1.0) nano-photocatalysts: synthesis, characterization and photocatalytic degradation of methylene blue dye. Journal of Molecular Structure. 2016; 1119:39-47; Silambarasu A, Manikandan A, Balakrishnan K. Room-Temperature Superparamagnetism and Enhanced Photocatalytic Activity of Magnetically Reusable Spinel ZnFe$_2$O$_4$ Nanocatalysts. Journal of Superconductivity and Novel Magnetism. 2017; 30(9):2631-40; and Suguna S, Shankar S, Jaganathan S K, Manikandan A. Novel synthesis of spinel Mn$_x$Co$_{1-x}$Al$_2$O$_4$ (x=0.0 to 1.0) nanocatalysts: effect of Mn$^{2+}$ doping on structural, morphological, and opto-magnetic properties. Journal of Superconductivity and Novel Magnetism. 2017; 30(3):691-9, each incorporated herein by reference in their entirety]. The significant Fe—O vibrational mode clearly demonstrated the existence of strong Cr doping in CuFe$_2$O$_4$ spinel lattice [Teresita V M, Manikandan A, Josephine B A, Sujatha S, Antony S A. Electromagnetic Properties and Humidity-Sensing Studies of Magnetically Recoverable LaMg$_x$Fe$_{1-x}$O$_{3-\delta}$ Perovskites Nano-photocatalysts by Sol-Gel Route. Journal of Superconductivity and Novel Magnetism. 2016, 29(6):1691-701; and Josephine B A, Manikandan A, Teresita V M, Antony S A. Fundamental study of LaMg$_x$Cr$_{1-x}$O$_{3-\delta}$ perovskites nano-photocatalysts: Sol-gel synthesis, characterization and humidity sensing. Korean Journal of Chemical Engineering. 2016; 33(5):1590-8, each incorporated herein by reference in their entirety].

EXAMPLE 5

UV-Visible Diffuse Reflectance Spectroscopy Analysis

Figure 3A:
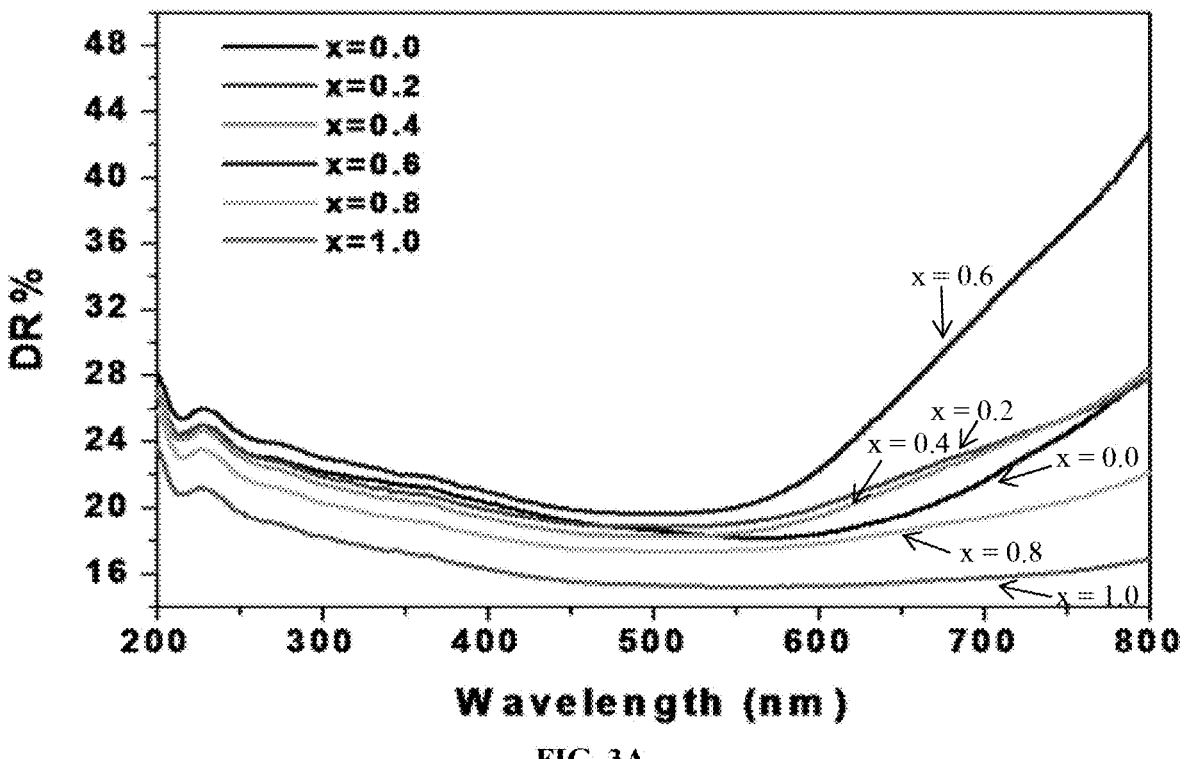
FIG. 3A is an overlay of diffuse reflectance (DR) spectra of spinel ferrite nanoparticles containing $CuCrFeO_4$ (x=1), $CuCr_{0.8}Fe_{1.2}O_4$ (x=0.8), $CuCr_{0.6}Fe_{1.4}O_4$ (x=0.6), $CuCr_{0.4}Fe_{1.6}O_4$ (x=0.4), $CuCr_{0.2}Fe_{1.8}O_4$ (x=0.2), and $CuFe_2O_4$ (x=0.0), respectively.
Figure 3B:
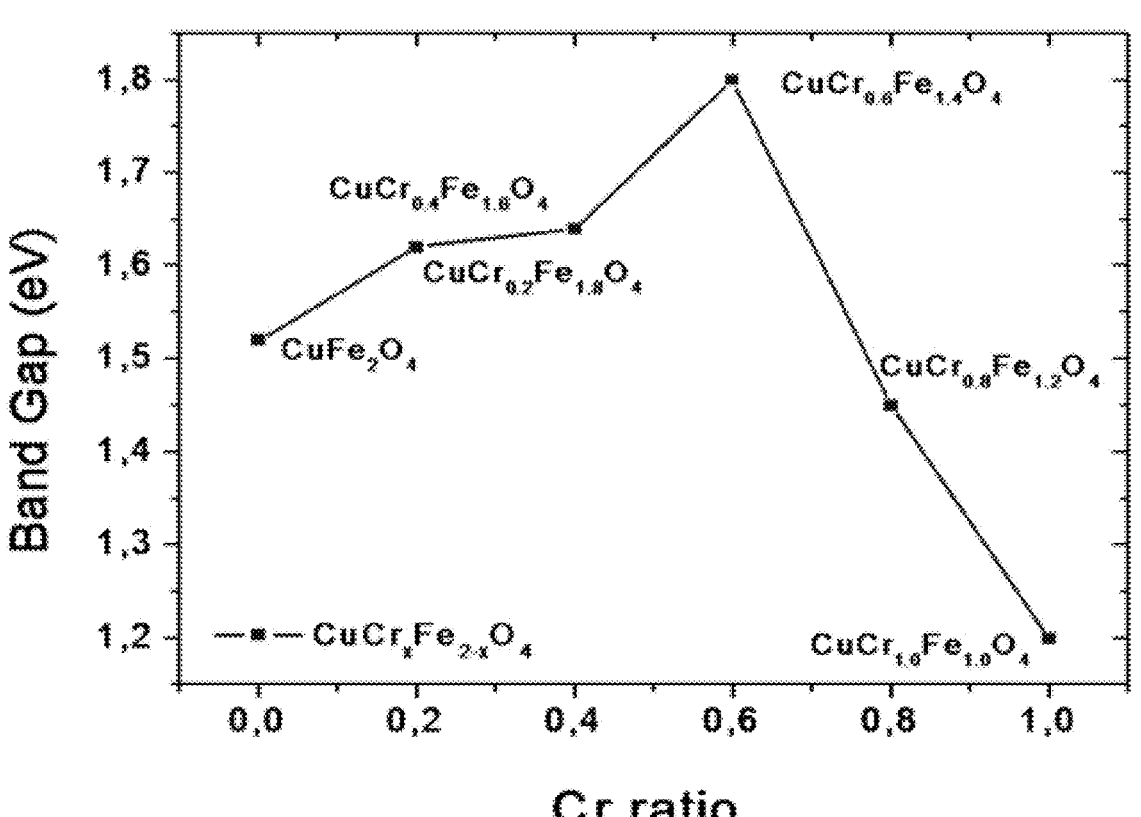
FIG. 3B shows band gap energy values of spinel ferrite nanoparticles containing $CuCrFeO_4$ (x=1), $CuCr_{0.8}Fe_{1.2}O_4$ (x=0.8), $CuCr_{0.6}F_{1.4}O_4$ (x=0.6), $CuCr_{0.4}Fe_{1.6}O_4$ (x=0.4), $CuCr_{0.2}Fe_{1.8}O_4$ (x=0.2), and $CuFe_2O_4$ (x=0.0), respectively.

The optical properties of spinel CuCr$_x$Fe$_{2-x}$O$_4$ (0.0≤x≤1.0) NPs were investigated by UV-vis percent diffuse reflectance (DR %) spectroscopy. The recorded spectra had a sweep range of 200-800 nm (FIG. 3A). All samples absorbed at least 72% or more of the light from 200 to 600 nm range. Above 600 nm, DR remarkably increased at different magnitudes depending on doped Cr ratio. Cr ratio dependent band gaps ($E_g$) were shown in FIG. 3B. The $E_g$ values were found in the range of 1.20 eV to 1.80 eV for $CuCr_xFe_{2-x}O_4$ (x=0.0, 0.2, 0.4, 0.6, 0.8, 1.0) NPs (FIG. 3B). The estimated band gap value increased from 1.52 eV of $CuFe_2O_4$ to a maximum of 1.80 eV for x=0.6, and a sharp decrease to a minimum of 1.20 eV for x=1.0 (FIG. 3B), which might be due to the smaller particle size.

EXAMPLE 6

Figure 4:
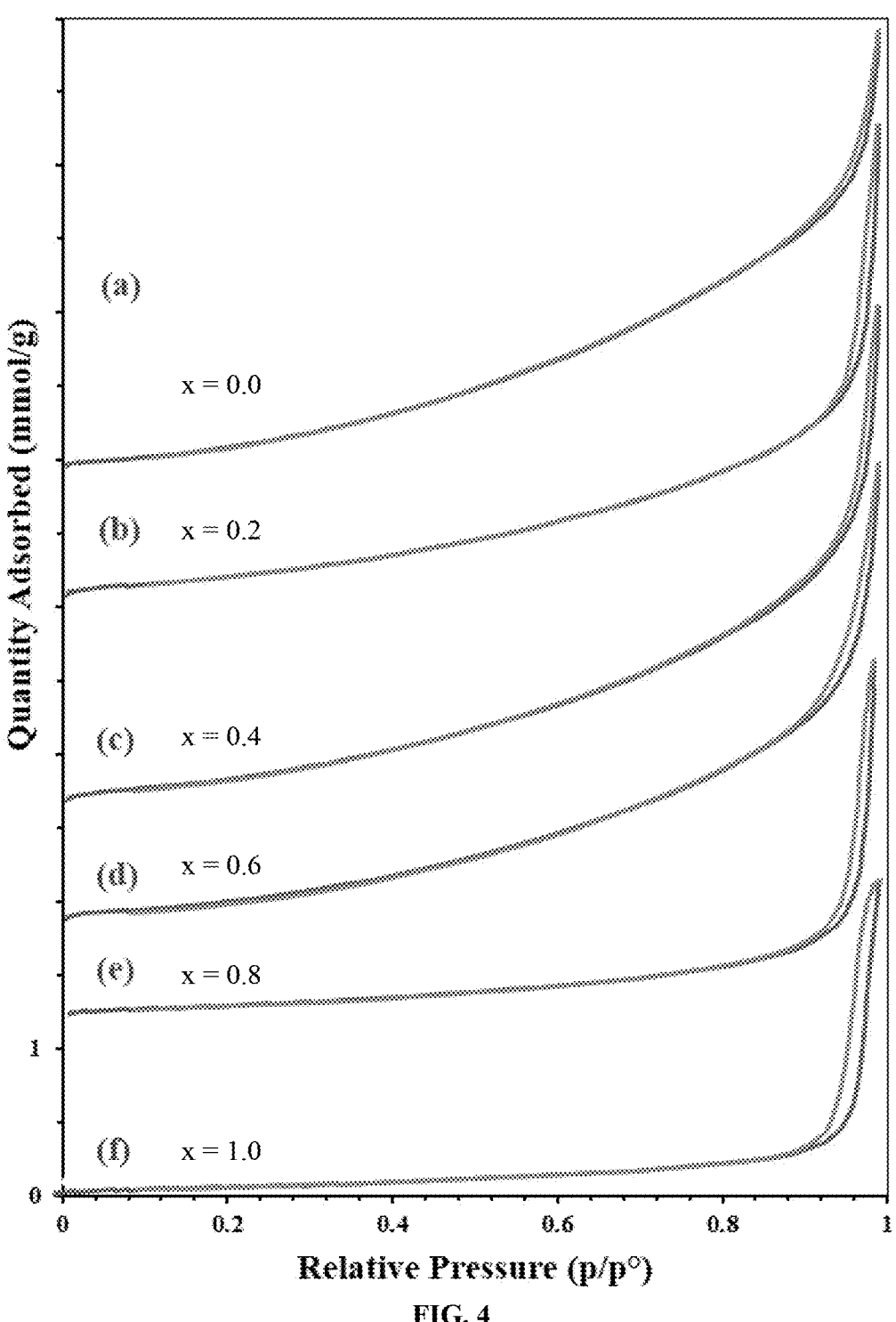
FIG. 4 is an overlay of nitrogen physisorption isotherm plots of spinel ferrite nanoparticles containing $CuCrFeO_4$ (x=1), $CuCr_{0.8}Fe_{1.2}O_4$ (x=0.8), $CuCr_{0.6}Fe_{1.4}O_4$ (x=0.6), $CuCr_{0.4}Fe_{1.6}O_4$ (x=0.4), $CuCr_{0.2}Fe_{1.8}O_4$ (x=0.2), and $CuFe_2O_4$ (x=0.0), respectively.
Figure 5A:
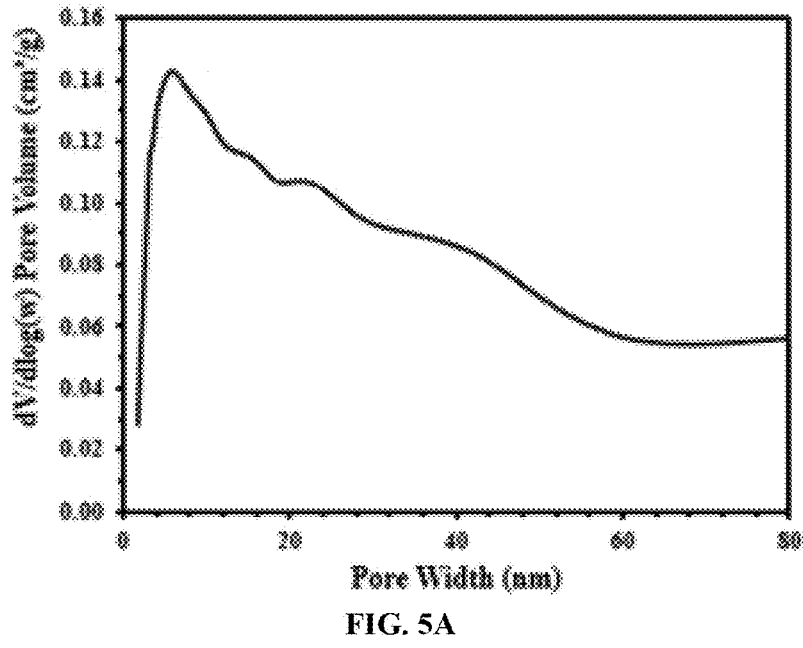
FIG. 5A shows pore size distribution of spinel ferrite nanoparticles containing $CuFe_2O_4$ (x=0.0).
Figure 5B:
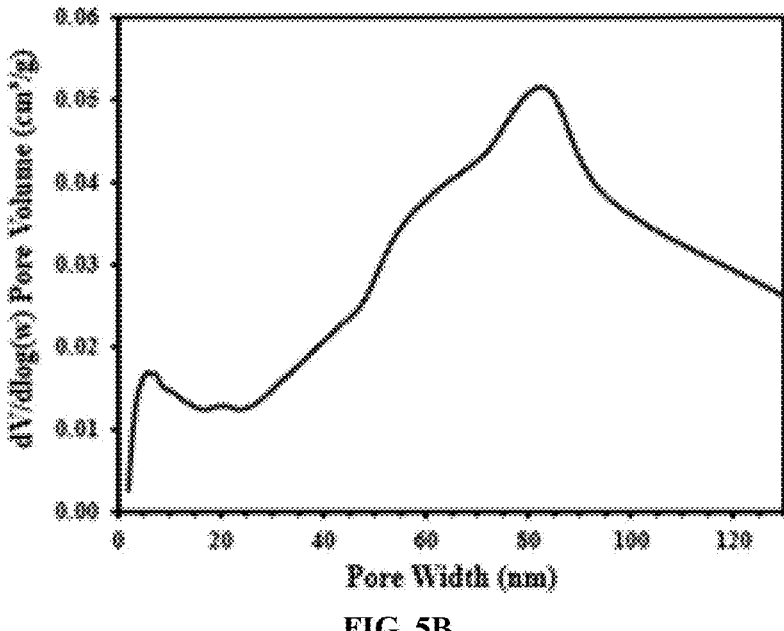
FIG. 5B shows pore size distribution of spinel ferrite nanoparticles containing $CuCr_{0.2}Fe_{1.8}O_4$ (x=0.2).
Figure 5C:
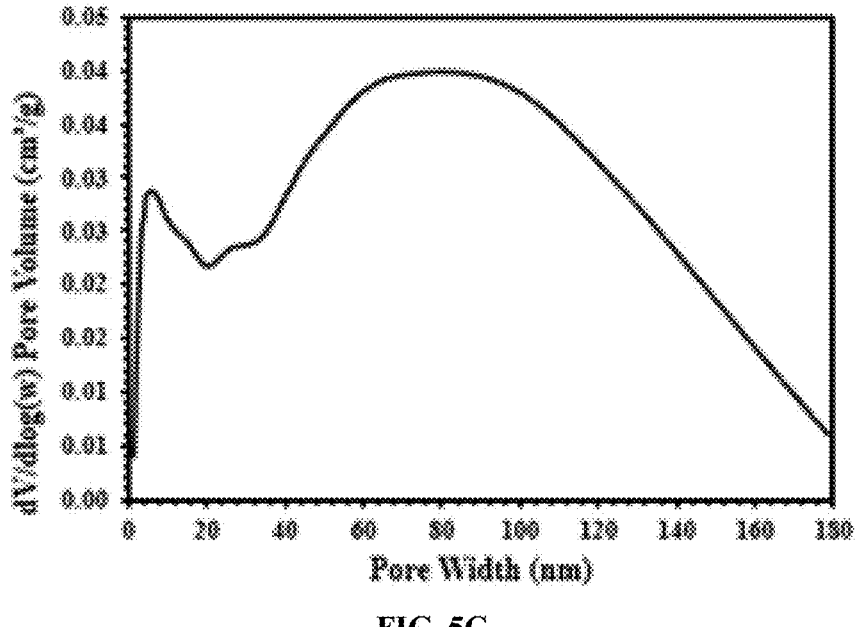
FIG. 5C shows pore size distribution of spinel ferrite nanoparticles containing $CuCr_{0.4}Fe_{1.6}O_4$ (x=0.4).
Figure 5D:
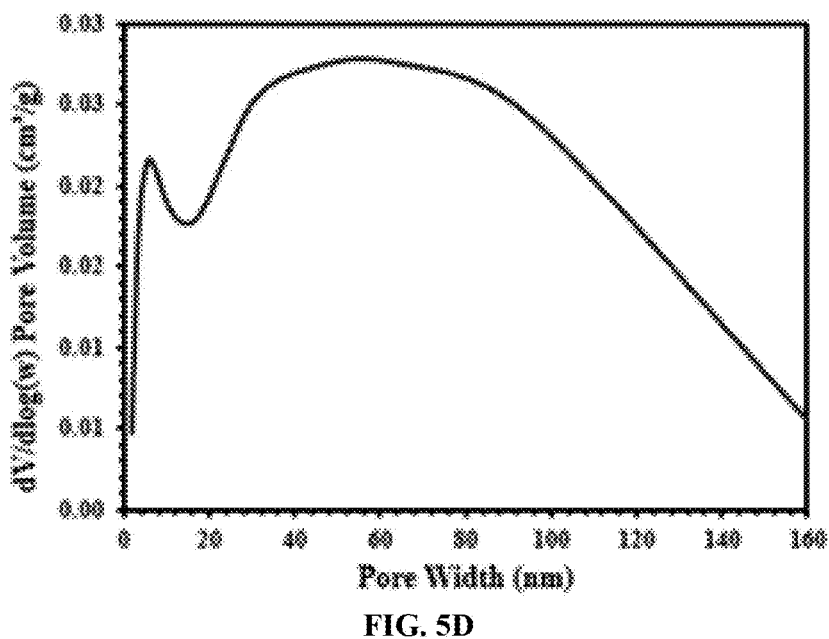
FIG. 5D shows pore size distribution of spinel ferrite nanoparticles containing $CuCr_{0.6}Fe_{1.4}O_4$ (x=0.6).
Figure 5E:
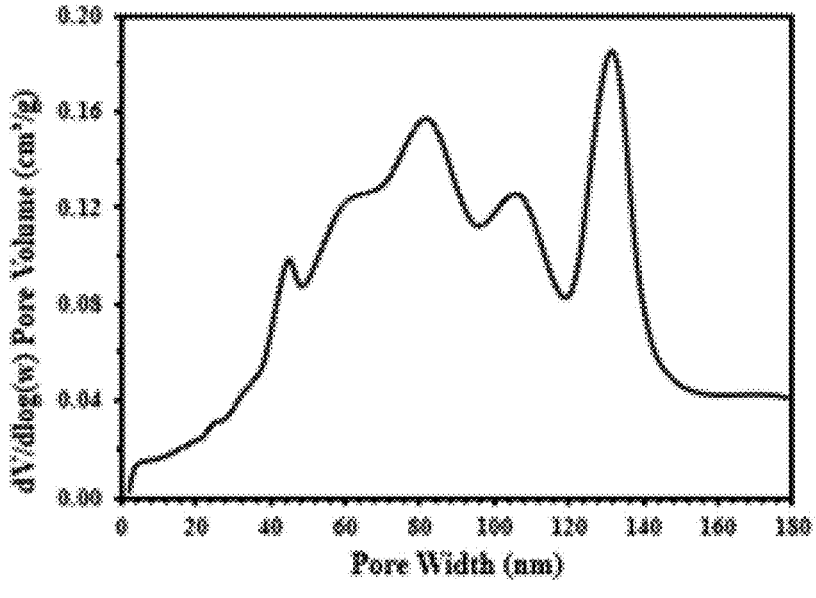
FIG. 5E shows pore size distribution of spinel ferrite nanoparticles containing $CuCr_{0.8}Fe_{1.2}O_4$ (x=0.8).
Figure 5F:
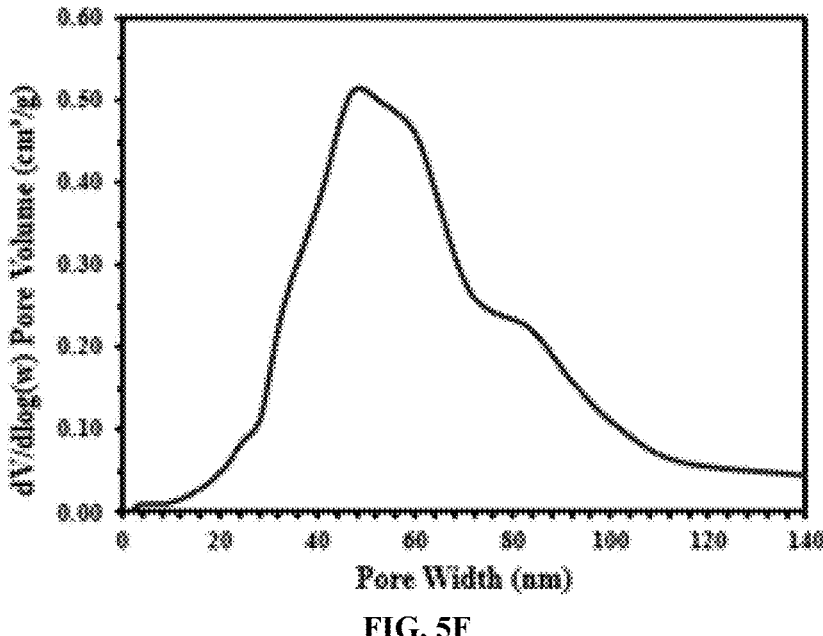
FIG. 5F shows pore size distribution of spinel ferrite nanoparticles containing $CuCrFeO_4$ (x=1).
Figure 6A:
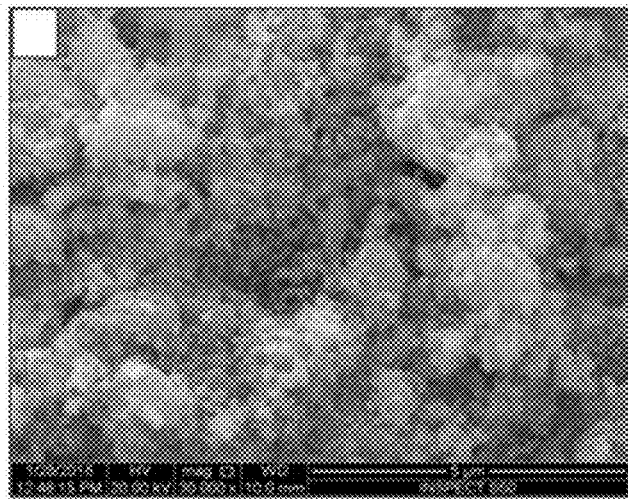
FIG. 6A is a scanning electron microscope (SEM) image of spinel ferrite nanoparticles containing $CuFe_2O_4$ (x=0.0).
Figure 6B:
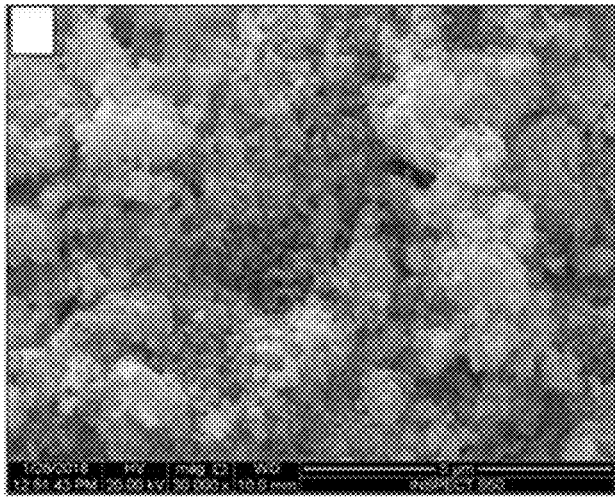
FIG. 6B is an SEM image of spinel ferrite nanoparticles containing $CuCr_{0.2}Fe_{1.8}O_4$ (x=0.2).
Figure 6C:
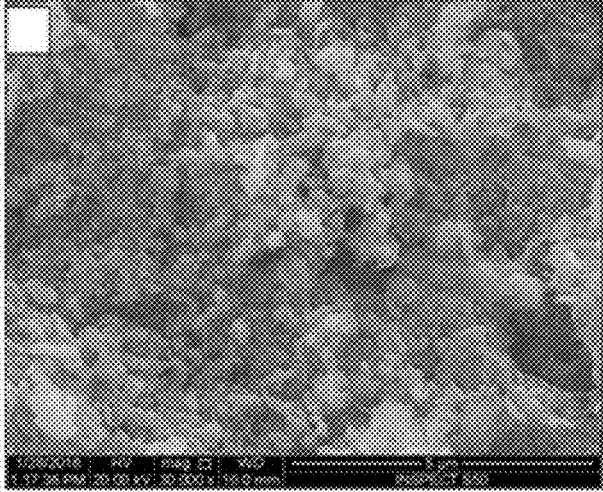
FIG. 6C is an SEM image of spinel ferrite nanoparticles containing $CuCr_{0.4}Fe_{1.6}O_4$ (x=0.4).
Figure 6D:
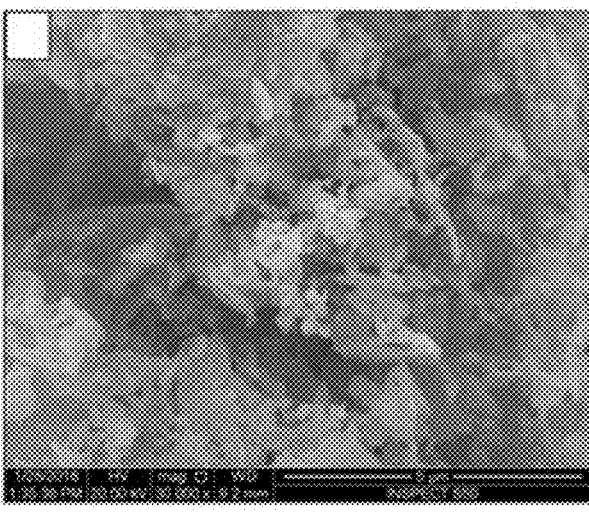
FIG. 6D is an SEM image of spinel ferrite nanoparticles containing $CuCr_{0.6}Fe_{1.4}O_4$ (x=0.6).
Figure 6E:
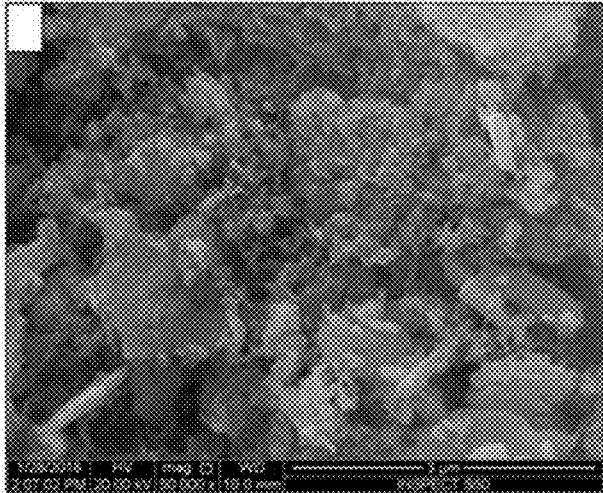
FIG. 6E is an SEM image of spinel ferrite nanoparticles containing $CuCr_{0.8}Fe_{1.2}O_4$ (x=0.8).
Figure 6F:
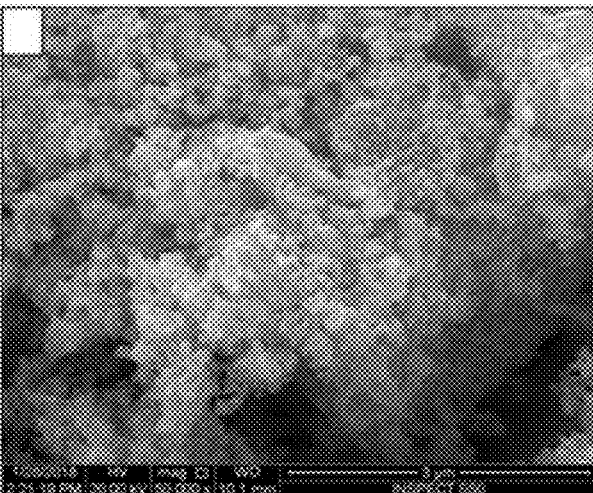
FIG. 6F is an SEM image of spinel ferrite nanoparticles containing $CuCrFeO_4$ (x=1).

Analysis of Surface Area and Pore Size Distribution: BET and BJH Measurements $N_2$ adsorption/desorption isotherms (BET) and BJH desorption pore size distribution plots of the synthesized spinel Cr substituted ferrite nanoparticles were shown in FIG. 4 and FIG. 5, respectively. Over the last three decades, BET analysis has been used to measure the specific surface area and texture of a wide range of porous materials [Sing K. The use of nitrogen adsorption for the characterization of porous materials. Colloids and Surfaces A: Physicochemical and Engineering Aspects 187-188 (2001) 3-9]. The isotherm curves of all samples showed a typical Langmuir IV type, with hysteresis according to IUPAC classification, disclosing the existence of a mesoporous structure [Ashour A H, El-Batal A I, Abdel Maksoud M I A, El-Sayyad G S, Labibc S, Abdeltwab E, El-Okr M M. Antimicrobial activity of metal-substituted cobalt ferrite nanoparticles synthesized by sol-gel technique. Particuology. 2018; volume 40, pages 141-151]. The BET surface area of Cr substituted ferrite nanoparticles decreased as Cr content increased, which might be attributed to the increase in grain size (Table 2). FIG. 5 shows the BJH desorption average pore diameter ($d_p$) of Cr substituted ferrite nanoparticles and it was observed that the pore diameter increased going from $CuFe_2O_4$ to $CuCrFeO_2$ (FIG. 5). Various textural and structural properties of synthesized spinel ferrite nanoparticles were summarized in Table 2.

of the synthesized Cr-substituted copper ferrite nanoparticles (A) $CuFe_2O_4$, (B) $CuCr_{0.2}Fe_{1.8}O_4$, (C) $CuCr_{0.4}Fe_{1.6}O_4$, (D) $CuCr_{0.6}Fe_{1.4}O_4$, (E) $CuCr_{0.8}Fe_{1.2}O_4$, and (F) $CuCrFeO_4$). The $CuFe_2O_4$ (FIG. 6A), $CuCr_{0.2}Fe_{1.8}O_4$ (FIG. 6B), and $CuCrFeO_4$ (FIG. 6F) nanoparticles exhibit spherical morphology. While FIGS. 6C-E present particles with angular, spinel, and irregular shapes. The average particle sizes of $CuFe_2O_4$, (B) $CuCr_{0.2}Fe_{1.8}O_4$, (C) $CuCr_{0.4}Fe_{1.6}O_4$, (D) $CuCr_{0.6}Fe_{1.4}O_4$, (E) $CuCr_{0.8}Fe_{1.2}O_4$ and (F) $CuCrFeO_4$ were ~65.0, ~73.5, ~47.6, ~69.9, 54.2 and ~28.0 nm, respectively. The SEM micrographs showed that the samples were porous in nature, with porosities observed between 22-25% as confirmed by XRD.

EXAMPLE 8

Characterizations of Antibacterial Activity of Spinel Nanoparticles

*E. coli* were chosen as model Gram-negative bacteria to investigate the antibacterial properties of $CuCr_xFe_{2-x}O_4$ (0.0≤x≤1.0) NPs. *E. coli* cultures were grown overnight in nutrient broth medium in a shaking incubator (200 rpm) at 37° C. The bacterial culture was then washed 2-3 times with phosphate buffered saline and the *E. coli* suspensions were diluted with sterile 0.9% NaCl solution to reach a final concentration of approximately $10^7$ CFU/mL.

EXAMPLE 9

Minimal Inhibitory Concentration (MIC)

The antibacterial activity of $CuCr_xFe_{2-x}O_4$ (0.0≤x≤1.0) NPs was assessed using the standard agar dilution method as previously described [Ansari M A, Khan H M, Alzohairy M A, Jalal M, Ali S G, Pal R, Musarrat J. Green synthesis of Al2O3 nanoparticles and their bactericidal potential against clinical isolates of multi-drug resistant *Pseudomonas aeruginosa*. World Journal of Microbiology and Biotechnology. 2015, 31(1):153-64]. The MIC was determined on MHA (Mueller Hinton Agar) plates using serial dilutions of $CuCr_xFe_{2-x}O_4$ (0.0≤x≤1.0) NPs at concentration ranges from

TABLE 2

| | | | | | | | | | |
|---|---|---|---|---|---|---|---|---|---|
| Surface properties of the spinel ferrite nanoparticles | | | | | | | | | |
| Sample | x | $S_{BET}$ ($m^2g^{-1}$) | $S_{micro}$[a] ($m^2g^{-1}$) | $S_{meso}$[b] ($m^2g^{-1}$) | $V_t$[c] ($cm^3g^{-1}$) | $V_{micro}$[a] ($cm^3g^{-1}$) | $d_p$[d] (nm) | APS[e] (nm) | HF[f] |
| $CuFe_2O_4$ | 0 | 19.6 | 1.5 | 18.1 | 0.02 | 0.02 | 8.7 | 65.0 | 0.92 |
| $CuCr_{0.2}Fe_{1.8}O_4$ | 0.2 | 18.8 | 1.7 | 17.1 | 0.019 | 0.01 | 12.4 | 73.5 | 0.47 |
| $CuCr_{0.4}Fe_{1.6}O_4$ | 0.4 | 14 | 1.1 | 12.9 | 0.03 | 0.01 | 10.4 | 47.6 | 0.31 |
| $CuCr_{0.6}Fe_{1.4}O_4$ | 0.6 | 13.5 | 1.0 | 12.5 | 0.02 | 0.01 | 11 | 69.9 | 0.46 |
| $CuCr_{0.8}Fe_{1.2}O_4$ | 0.8 | 11.1 | 0.8 | 10.3 | 0.02 | 0.03 | 10.7 | 54.2 | 1.4 |
| $CuCrFeO_4$ | 1 | 10.5 | 0.6 | 9.9 | 0.03 | 0.03 | 14.5 | 28.0 | 0.94 |

[a]Micropore area/volume calculated using the t-plot;
[b]External surface area calculated using the t-plot;
[c]Total pore volume adsorbed at $p/p^0 = 0.95$;
[d]BJH Adsorption average pore width (4V/A);
[e]Average particle size (APS);
[f]Hierarchical factor (HF), HF = $(V_{micro}/V_{total})$ * $(S_{meso}/S_{BET})$

EXAMPLE 7

Scanning Electron Microscopy Analysis

The morphology of nanoparticles of $CuCr_xFe_{2-x}O_4$ ferrites was examined by SEM. FIG. 6 shows the SEM images 32 mg/ml to 0.5 mg/mL. The MIC is determined as the lowest concentration of NPs at which no visible growth of the bacteria was observed [Ansari M A, Khan H M, Alzohairy M A, Jalal M, Ali S G, Pal R, Musarrat J. Green synthesis of Al2O3 nanoparticles and their bactericidal potential against clinical isolates of multi-drug resistant

*Pseudomonas aeruginosa.* World Journal of Microbiology and Biotechnology. 2015, 31(1):153-64].

EXAMPLE 10

Minimal Bactericidal Concentration (MBC)

The concentrations of $CuCr_xFe_{2-x}O_4$ ($0.0 \leq x \leq 1.0$) NPs showed effective inhibition of bacteria growth were selected for MBC examination [Jalal M, Ansari M A, Shukla A K, Ali S G, Khan H M, Pal R, Alam J, Cameotra S S. Green synthesis and antifungal activity of $Al_2O_3$ NPs against fluconazole-resistant *Candida* spp isolated from a tertiary care hospital. RSC Advances. 2016, 6(109):107577-90]. Briefly, 100 μL 0.9% normal saline were added onto the MIC plates, which was transferred to another freshly prepared MHA plate and then incubated at 37° C. for 24 h [Jalal et al. 2016]. The lowest concentration of $CuCr_xFe_{2-x}O_4$ ($0.0 \leq x \leq 1.0$) NPs at which no growth of bacterial cells found or less than three CFUs present was recorded as MBC [Jalal et al. 2016].

EXAMPLE 11

Effect of Spinel Ferrite Nanoparticles on the Morphology of *E. coli*: SEM Analysis The antibacterial effect of $CuCr_xFe_{2-x}O_4$ ($0.0 \leq x \leq 1.0$) NPs on the morphology of *E. coli* cells was investigated by scanning electron microscope using previously reported methods [Ansari M A, Khan H M, Alzohairy M A, Jalal M, Ali S G, Pal R, Musarrat J. Green synthesis of $Al_2O_3$ nanoparticles and their bactericidal potential against clinical isolates of multi-drug resistant *Pseudomonas aeruginosa*. World Journal of Microbiology and Biotechnology. 2015, 31(1):153-64; and Jalal M, Ansari M A, Shukla A K, Ali S G, Khan H M, Pal R, Alam J, Cameotra S S. Green synthesis and antifungal activity of $Al_2O_3$ NPs against fluconazole-resistant *Candida* spp isolated from a tertiary care hospital. RSC Advances. 2016, 6(109):107577-90]. Briefly, ~$10^6$ CFU/mL of *E. coli* cells were treated with 2 mg/mL of $CuCr_xFe_{2-x}O_4$ ($0.0 \leq x \leq 1.0$) NPs at 37° C. for 12 h. After centrifugation at 12000 rpm for 10 min, pellets were obtained and then washed at least three times with PBS, initially fixed with 2.5% glutaraldehyde, and further fixed with 1% osmium tetroxide. After washing, the samples were dehydrated by a series of ethanol solvent [Ansari M A, Khan H M, Alzohairy M A, Jalal M, Ali S G, Pal R, Musarrat J. Green synthesis of $Al_2O_3$ nanoparticles and their bactericidal potential against clinical isolates of multi-drug resistant *Pseudomonas aeruginosa*. World Journal of Microbiology and Biotechnology. 2015, 31(1):153-64; and Jalal M, Ansari M A, Shukla A K, Ali S G, Khan H M, Pal R, Alam J. Cameotra S S. Green synthesis and antifungal activity of $Al_2O_3$ NPs against fluconazole-resistant *Candida* spp isolated from a tertiary care hospital. RSC Advances. 2016, 6(109):107577-90]. The cells were then fixed on the aluminum stubs, dried in a desecrator, and coated with gold to prepare SEM samples. Finally, these samples were examined at an accelerating voltage of 20 kV by SEM.

EXAMPLE 12

Antibacterial Activity of Chromium-Substituted Copper Ferrite Nanoparticles

In the present disclosure, antibacterial properties of chromium-substituted copper ferrite nanoparticles against *E. coli*

(ATCC 25922) have been evaluated by determining MICs and MBCs using agar dilution methods. The MICs and MBCs values of spinel $CuCr_xFe_{2-x}O_4$ (x=0.0, 0.2, 0.4, 0.6, 0.8, 1.0) nanoparticles were summarized in Table 3. The lowest MIC and MBC values recorded were 2.5 and 5 mg/mL for $CuCr_{0.4}Fe_{1.6}O_4$. $CuCr_{0.8}Fe_{1.2}O_4$ and $CuCrFeO_4$ nanoparticles, whereas $CuFe_2O_4$ and $CuCr_{0.2}Fe_{1.8}O_4$ nanoparticles showed larger MIC and MBC values, i.e., >16 and >32 mg/mL. In a recent study, Ashour et al. [Ashour A H, El-Batal A I, Abdel Maksoud M I A, El-Sayyad G S, Labibc S, Abdeltwab E, El-Okr M M. Antimicrobial activity of metal-substituted cobalt ferrite nanoparticles synthesized by sol-gel technique. Particuology. 2018; volume 40, pages 141-151, incorporated herein by reference in its entirety] reported that metal-substituted cobalt ferrite nanoparticles such as copper cobalt ferrite, zinc cobalt ferrite and manganese cobalt ferrite inhibited growth of *E. coli* and *S. aureus* at a concentration of 5000 ppm. It has also been found that as the content of dopant (Cr) increased from 0.0 to 1.0, the antibacterial activity of ferrite nanoparticles also increased (Table 3). In a previous study, it was reported that the bactericidal activity of copper-substituted cobalt ferrite nanoparticles enhanced when the content of Cu increased [Samavati A, Ismail A F. Antibacterial properties of copper-substituted cobalt ferrite nanoparticles synthesized by co-precipitation method. Particuology. 2017; 30:158-63, incorporated herein by reference in its entirety]. Further, it was observed that the $CuCr_xFe2_{-x}O_4$ nanoparticles inhibited bacterial growth in a size dependent manner i.e., smaller size $CuCr_xFe_{2-x}O_4$ (20.2 nm; x=1.0) nanoparticles exhibited stronger antibacterial activity and inhibited bacterial growth at lower concentrations i.e., 2.5 mg/mL, whereas larger size $CuCr_xFe_{2-x}O_4$ nanoparticles (43.3 nm; x=0.0) inhibited bacterial growth at higher concentrations i.e., >16 mg/mL (Table 3). Results on size dependent antimicrobial activity of chromium substituted copper ferrite nanoparticles were in good agreement of previous study by Žalnėravičius et al. [Žalnėravičius R. Paškevičius A. Kurtinaitiene M. Jagminas A. Size-dependent antimicrobial properties of the cobalt ferrite nanoparticles. Journal of Nanoparticle Research. 2016, 18(10):300, incorporated herein by reference in its entirety], where they also reported size dependent antimicrobial activity of cobalt ferrite nanoparticles. Size dependent antimicrobial activity has also been reported for metal oxide nanoparticles such as ZnO [Raghupathi K R, Koodali R T, Manna A C. Size-dependent bacterial growth inhibition and mechanism of antibacterial activity of zinc oxide nanoparticles. Langmuir. 2011, 27(7):4020-8, incorporated herein by reference in its entirety] and CuO [She B, Wan X, Tang J, Deng Y, Zhou X, Xiao C. Size- and Morphology-Dependent Antibacterial Properties of Cuprous Oxide Nanoparticle and Their Synergistic Antibacterial Effect. Science of Advanced Materials. 2016, 8(5):1074-8, incorporated herein by reference in its entirety]. The content of chromium ions (factor of x=0.2) in the outer part of copper ferrite NP shell and effect on number of smaller sized particles was disclosed [Žalnėravičius R, Paškevičius A, Kurtinaitiene M, Jagminas A. Size-dependent antimicrobial properties of the cobalt ferrite nanoparticles. Journal of Nanoparticle Research. 2016, 18(10):300, incorporated herein by reference in its entirety].

27

TABLE 3

MIC and MBC (mg/mL) values of chromium-substituted copper
ferrite nanoparticles ($CuCr_xFe_{2-x}O_4$ where
x = 0.0, 0.2, 0.4, 0.6, 0.8, and 1.0) against *E. coli*

| Chromium-substituted copper ferrite nanoparticles | Crystallite size (nm) | MIC (mg/mL) | MBC (mg/mL) | MBC/MIC ratio |
|---|---|---|---|---|
| $CuFe_2O_4$ | 43.33 | >16 | >32 | >2 |
| $CuCr_{0.2}Fe_{1.8}O_4$ | 25.65 | >16 | >32 | >2 |
| $CuCr_{0.4}Fe_{1.6}O_4$ | 34.58 | 2.5 | 5 | 2 |
| $CuCr_{0.6}Fe_{1.4}O_4$ | 27.54 | 4 | 8 | 2 |
| $CuCr_{0.8}Fe_{1.2}O_4$ | 22.98 | 2.5 | 5 | 2 |
| $CuCrFeO_4$ | 20.21 | 2.5 | 5 | 2 |

EXAMPLE 13

Figure 7A:
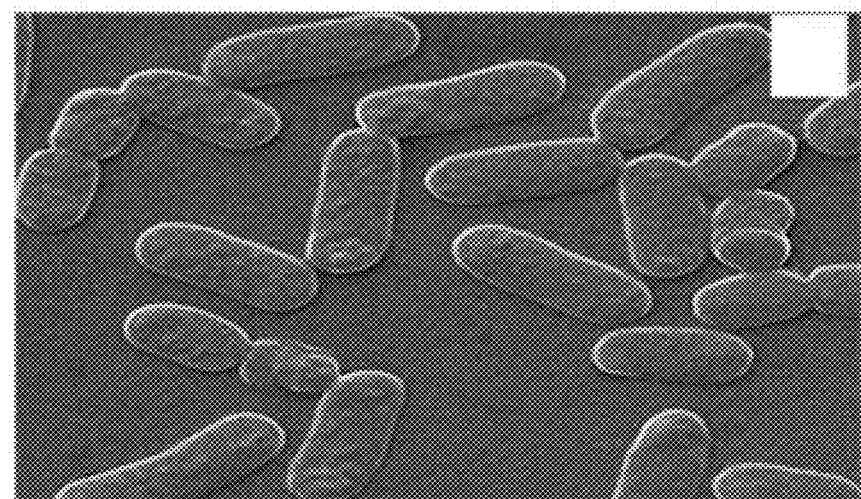
FIG. 7A is an SEM image of *Escherichia coli* cells.
Figure 7B:
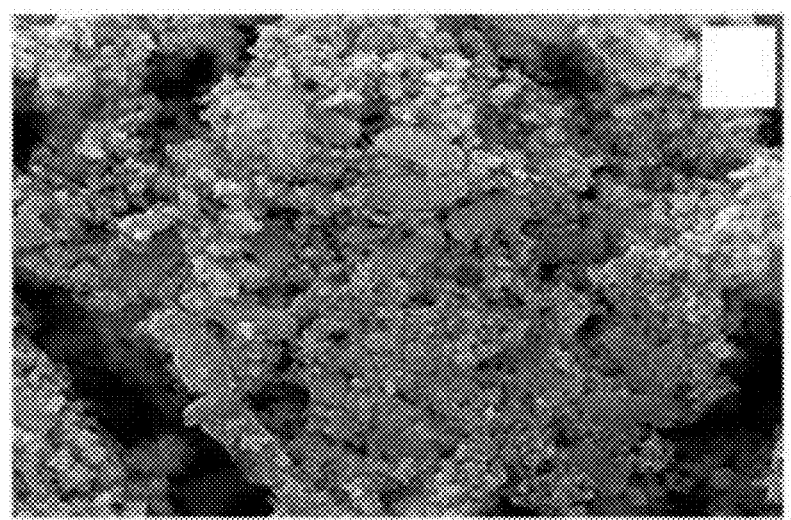
FIG. 7B is an SEM image of *Escherichia coli* cells treated with spinel ferrite nanoparticles containing $CuFe_2O_4$.
Figure 7C:
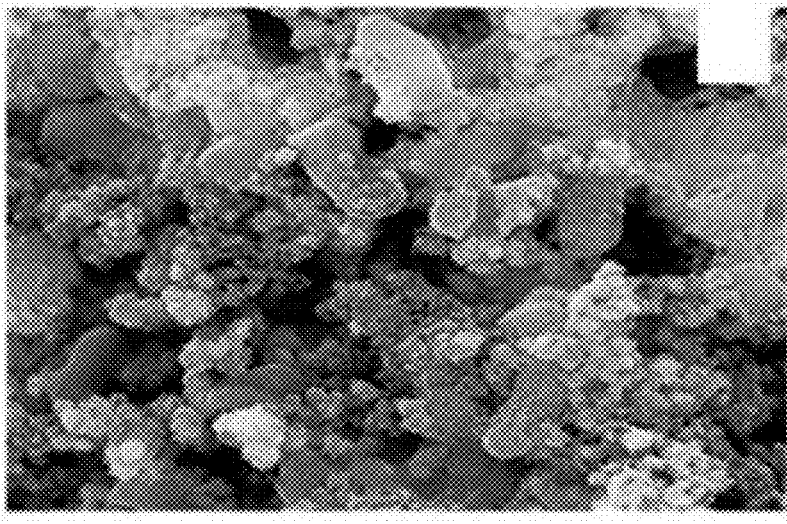
FIG. 7C is an SEM image of *Escherichia coli* cells treated with spinel ferrite nanoparticles containing $CuCr_{0.2}Fe_{1.8}O_4$.
Figure 7D:
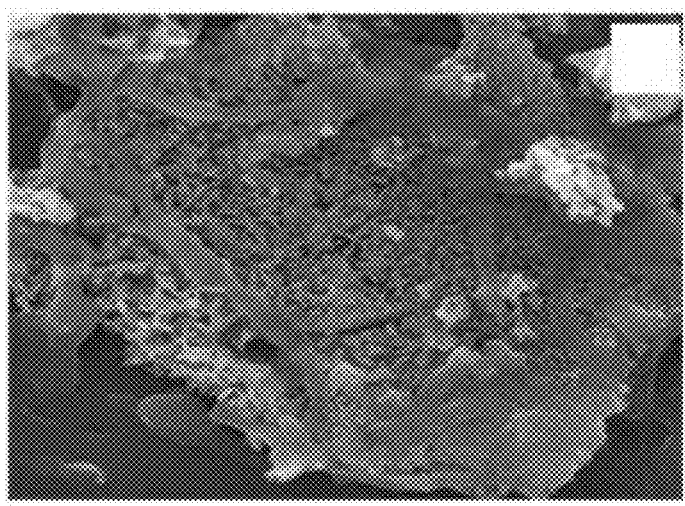
FIG. 7D is an SEM image of *Escherichia coli* cells treated with spinel ferrite nanoparticles containing $CuCr_{0.5}Fe_{1.6}O_4$.
Figure 7E:
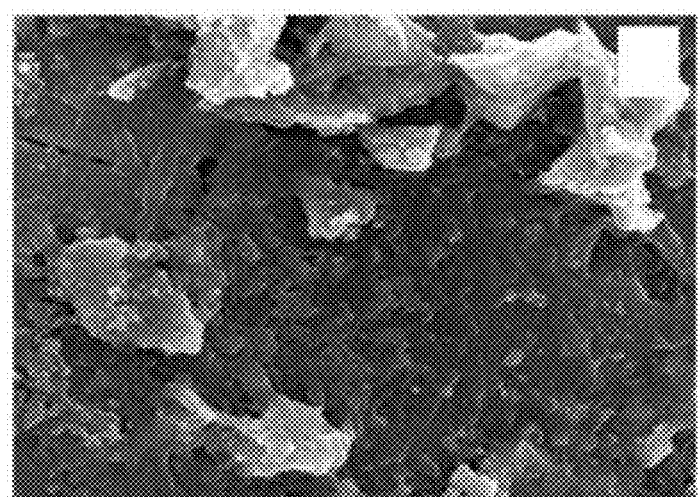
FIG. 7E is an SEM image of *Escherichia coli* cells treated with spinel ferrite nanoparticles containing $CuCr_{0.6}Fe_{1.4}O_4$.
Figure 7F:
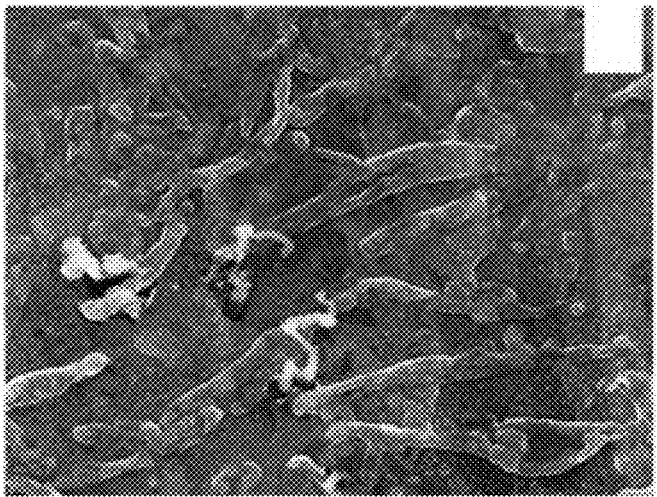
FIG. 7F is an SEM image of *Escherichia coli* cells treated with spinel ferrite nanoparticles containing $CuCr_{0.8}Fe_{1.2}O_4$.
Figure 7G:
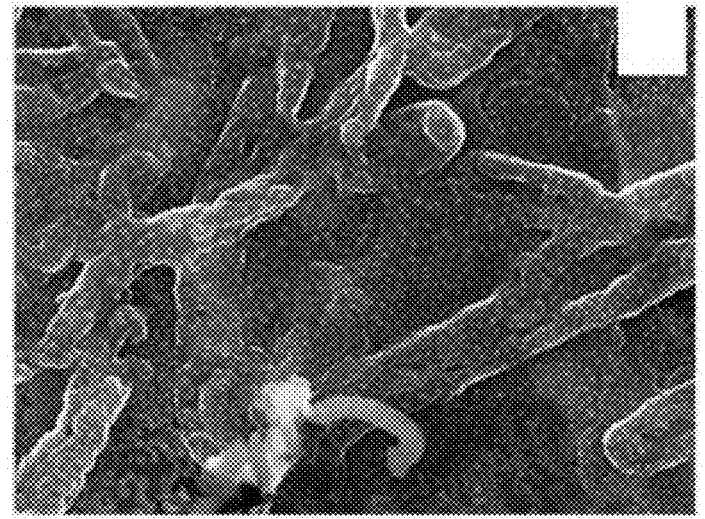
FIG. 7G is an SEM image of *Escherichia coli* cells treated with spinel ferrite nanoparticles containing $CuCrFeO_4$.

Effects of $CuCr_xFe_{2-x}O_4$ Nanoparticles on the Morphology of *E. coli*: SEM Analysis The morphological and structural changes in *E. coli* cells caused by chromium-substituted copper ferrite nanoparticles were further investigated by SEM. The untreated (i.e., control) *E. coli* cells were typically rod-shaped and regular with a smooth cell surface. Cell wall and cell membrane of untreated *E. coli* cells were normal and intact (FIG. 7A). However, *E. coli* cells treated with $CuCr_xFe_{2-x}O_4$ nanoparticles were not intact i.e., abnormal in shape with irregular fragments appeared at the cell surface (FIGS. 7B-G). *E. coli* cells treated with the presently disclosed nanoparticles were severely damaged as pits, indentation, deformation, and distortion of cell wall and membrane were observed, which indicated that significant loss of membrane integrity might lead to cell death (FIGS. 7B-G). There is very little information available in the literature regarding the antimicrobial properties and mode of action of metal-substituted ferrite nanoparticles against bacteria [Sanpo N, Wen C, Berndt C C, Wang J. Antibacterial properties of spinel ferrite nanoparticles. Microbial pathogens and strategies for combating them: science, technology and education. Spain: Formatex Research Centre. 2013:239-50; and Samavati A, Ismail A F. Antibacterial properties of copper-substituted cobalt ferrite nanoparticles synthesized by co-precipitation method. Particuology. 2017; 30:158-63, each incorporated herein by reference in their entirety]. Previous reports on other nanoparticles against bacteria disclosed that morphological and structural alteration in the bacterial cell membrane due to nanoparticles attachment and penetration might be a possible mode of action [Jalal M, Ansari M A, Shukla A K, Ali S G, Khan H M, Pal R, Alam J, Cameotra S S. Green synthesis and antifungal activity of $Al_2O_3$ NPs against fluconazole-resistant *Candida* spp isolated from a tertiary care hospital. RSC Advances. 2016, 6(109):107577-90; Sondi I, Salopek-Sondi B. Silver nanoparticles as antimicrobial agent: a case study on *E. coli* as a model for Gram-negative bacteria. Journal of colloid and interface science. 2004, 275(1):177-82; Jiang W, Mashayekhi H, Xing B (2009) Bacterial toxicity comparison between nano- and micro-scale oxide particles. Environ Pollut 157:1619-1625; and Leung Y H, Xu X, Ma A P, Liu F, Ng A M, Shen Z, Gethings L A, Guo M Y, Djurišić A B, Lee P K, Lee H K. Toxicity of ZnO and $TiO_2$ to *Escherichia coli* cells. Scientific reports. 2016, 6:35243, each incorporated herein by reference in their entirety]. Thus, the attachments of NPs to bacterial cell surface might play an important role in achieving good bactericidal activity. From SEM images (FIGS. 7B-G), it was clear that $CuCr_xFe_{2-x}O_4$ nanoparticles were able to adhere to bacterial cell surfaces and damage the cell membrane due to interaction between nanoparticles and cell membrane [Jalal M, Ansari M A, Shukla A K, Ali S G, Khan H M, Pal R, Alam J, Cameotra S S. Green synthesis and antifungal activity of $Al_2O_3$ NPs against fluconazole-resistant *Candida* spp isolated from a tertiary care hospital. RSC Advances. 2016, 6(109):107577-90; and Leung Y H, Xu X, Ma A P, Liu F, Ng A M, Shen Z, Gethings L A, Guo M Y, Djurišić A B, Lee P K, Lee H K. Toxicity of ZnO and $TiO_2$ to *Escherichia coli* cells. Scientific reports. 2016, 6:35243, each incorporated herein by reference in their entirety]. Another possible mechanism reported in previous studies was the generation of reactive oxygen species (ROS) by nanoparticles. In the current disclosure, decomposition of $CuCr_xFe_{2-x}O_4$ nanoparticles may generate ROS that electrostatically interact with cell walls and cause damage to bacteria cells [Schwartz V B, Thétiot F, Ritz S, Pütz S, Choritz L, Lappas A. Förch R, Landfester K, Jonas U. Antibacterial surface coatings from zinc oxide nanoparticles embedded in poly (n-isopropylacrylamide) hydrogel surface layers. Advanced Functional Materials. 2012, 22(11):2376-86, incorporated herein by reference in its entirety]. The results were in good agreement with the previous study by Sanpo et al. [Sanpo N, Wen C, Berndt C C, Wang J. Antibacterial properties of spinel ferrite nanoparticles. Microbial pathogens and strategies for combating them: science, technology and education. Spain: Formatex Research Centre. 2013:239-50, incorporated herein by reference in its entirety], which reported that generation of ROS from spinel metal substituted cobalt ferrite nanoparticles had more potential to enter the cell wall and inhibit the growth of *E. coli* and *S. aureus*. In previous studies, ROS generated from the surface of NPs may have interacted with the cell membrane and damaged the membrane due to increased cell permeability and leakage of the intracellular materials [Leung Y H, Xu X, Ma A P, Liu F, Ng A M, Shen Z, Gethings L A, Guo M Y, Djurišić A B, Lee P K, Lee H K. Toxicity of ZnO and $TiO_2$ to *Escherichia coli* cells. Scientific reports. 2016, 6:35243; Schwartz V B, Thétiot F, Ritz S, Pütz S, Choritz L, Lappas A, Förch R, Landfester K, Jonas U. Antibacterial surface coatings from zinc oxide nanoparticles embedded in poly (n-isopropylacrylamide) hydrogel surface layers. Advanced Functional Materials. 2012, 22(11):2376-86; and Pandey B K, Shahi A K, Srivastava N, Kumar G, Gopal R (2015) Synthesis and cytogenetic effect of magnetic nanoparticles. Adv Mater Lett 6:954-960, each incorporated herein by reference in their entirety]. Tran et al. [Tran N, Mir A, Mallik D, Sinha A, Nayar A, Webster T J (2010) Bactericidal effect of iron oxide nanoparticles on *Staphylococcus aureus*. Int J Nanomed 5:277-283, incorporated herein by reference in its entirety] also reported that $Fe_2O_3$ NPs could penetrate bacterial cells and generate ROS. Further, as the concentration of dopant (Cr) increased in $CuCr_xFe_{2-x}O_4$ nanoparticles, smaller crystalline sized nanoparticles were obtained with a lager surface-to-volume ratio. A higher surface area of $CuCr_xFe_{2-x}O_4$ nanoparticles might enhance their antimicrobial activity and killing rates [Samavati A, Ismail A F. Antibacterial properties of copper-substituted cobalt ferrite nanoparticles synthesized by co-precipitation method. Particuology. 2017; 30:158-63; and Stoimenov P K, Klinger R L, Marchin G L, Klabunde K J. Metal oxide nanoparticles as bactericidal agents. Langmuir. 2002, 18(17):6679-86, each incorporated herein by reference in their entirety].

EXAMPLE 14

Chromium-substituted copper ferrite nanoparticles were prepared by co-precipitation method. All the chromium-substituted nanoparticles were spinel in structure. Substitution of chromium ions has influenced the crystal and microstructure of copper ferrite nanoparticles and enhanced their antibacterial property. Further, as the content of Cr ions increases from 0.0 to 1.0, the crystallite size of copper ferrite nanoparticles decreases from 43.3 to 20.2 nm. Size dependent antibacterial activity of chromium-substituted copper ferrite nanoparticles has been investigated for the first time. $CuCrFeO_4$ nanoparticles with smaller size (20.2 nm) exhibit MIC of 2.5 mg/mL, whereas larger size $CuFe_2O_4$ (43.3 nm) nanoparticles show MIC of >16 mg/mL. Because of their excellent antibacterial activity, Cr-substituted copper ferrite nanoparticles may be used in coating of medical devices to prevent microbial biofilm growth, magnetic drug delivery systems, as well as ointments, cosmetics, creams and lotions for topical application.

The invention claimed is:

1. A method for preventing or reducing growth of a microorganism on a surface, the method comprising:

applying spinel ferrite nanoparticles onto the surface and contacting the microorganism with the spinel ferrite nanoparticles to electrostatically damage cell walls of the microorganism;

wherein the spinel ferrite nanoparticles comprise a chromium-substituted copper ferrite of formula (I)

$$CuCr_xFe_{2-x}O_4 \tag{I}$$

wherein X is in a range of from 0.4 to 1;

wherein the spinel ferrite nanoparticles are in contact with the surface for a time in a range of from 0.1 to 24 hours; and wherein a count of the microorganism on the surface is reduced more by the chromium-substituted copper ferrite than a copper ferrite without chromium substitution.

2. The method of claim 1, wherein the spinel ferrite nanoparticles have an average particle size in a range of from 20 to 90 nm.

3. The method of claim 1, wherein the applying comprises applying a suspension comprising a solvent and the spinel ferrite nanoparticles in a range of from 50 to 100 mg/mL, relative to total suspension volume, onto the surface.

4. The method of claim 3, wherein the solvent comprises water.

5. The method of claim 1, wherein the microorganism is a gram-negative bacterium.

6. The method of claim 5, wherein the gram-negative bacterium is *Escherichia coli.*

7. The method of claim 1, wherein, in the chromium-substituted copper ferrite, $CuCr_xFe_{2-x}O_4$ (I), X is in a range of from 0.4 to 1.

8. The method of claim 1, wherein, in the chromium-substituted copper ferrite, $CuCr_xFe_{2-x}O_4$ (I), X is in a range of from 0.6 to 1.

9. The method of claim 1, wherein a count of the microorganism on the surface is reduced by at least 20% after the contacting.

10. The method of claim 1, wherein a count of the microorganism on the surface is reduced by at least 70% after the contacting.

11. The method of claim 1, wherein a count of the microorganism on the surface is reduced by at least 95% after the contacting.

12. The method of claim 1, wherein a count of the microorganism on the surface is reduced more by the chromium-substituted copper ferrite than a copper ferrite without chromium substitution.

* * * * *